(12) United States Patent
Joplin

(10) Patent No.: US 10,964,420 B2
(45) Date of Patent: *Mar. 30, 2021

(54) METHODS AND SYSTEMS FOR PALLET SIZING AND PUCKING

(71) Applicant: Express Scripts Strategic Development, Inc., St. Louis, MO (US)

(72) Inventor: Jonathan W. Joplin, Chesterfield, MO (US)

(73) Assignee: Express Scripts Strategic Development, Inc., St. Louis, MO (US)

(*) Notice: Subject to any disclaimer, the term of this patent is extended or adjusted under 35 U.S.C. 154(b) by 0 days.

This patent is subject to a terminal disclaimer.

(21) Appl. No.: 16/838,375

(22) Filed: Apr. 2, 2020

(65) Prior Publication Data

US 2020/0246966 A1    Aug. 6, 2020

Related U.S. Application Data

(63) Continuation of application No. 16/118,630, filed on Aug. 31, 2018, now Pat. No. 10,639,786, which is a continuation of application No. 14/798,344, filed on Jul. 13, 2015, now Pat. No. 10,086,974.

(51) Int. Cl.
| | |
|---|---|
| *B65B 57/16* | (2006.01) |
| *G16H 20/13* | (2018.01) |
| *B65D 19/44* | (2006.01) |
| *B25J 9/00* | (2006.01) |
| *B25J 15/00* | (2006.01) |

(52) U.S. Cl.
CPC ............ *G16H 20/13* (2018.01); *B25J 9/0093* (2013.01); *B25J 15/0052* (2013.01); *B65B 57/16* (2013.01); *B65D 19/44* (2013.01)

(58) Field of Classification Search
CPC ......... B65B 21/06; B65B 35/36; B65B 5/103; B25J 15/0095; B65G 2201/0261; Y10S 53/90

See application file for complete search history.

(56) References Cited

U.S. PATENT DOCUMENTS

| | | |
|---|---|---|
| 4,395,069 A | 7/1983 | Lebret |
| 4,919,586 A | 4/1990 | Derby |
| 5,771,657 A | 6/1998 | Lasher |
| 6,363,687 B1 | 4/2002 | Luciano |
| 6,435,582 B1 | 8/2002 | Dasilva |
| 6,769,228 B1 | 8/2004 | Mahar |
| 6,857,174 B2 | 2/2005 | Morita |
| 6,892,512 B2 | 5/2005 | Rice |
| 7,313,898 B1 * | 1/2008 | Eller ...................... B65B 21/06 108/153.1 |

(Continued)

*Primary Examiner* — Gregory W Adams
(74) *Attorney, Agent, or Firm* — Dickinson Wright PLLC

(57) ABSTRACT

A pharmaceutical order filling system uses pucks disposed on a pallet to accommodate a plurality of container sizes into which pharmaceuticals can be dispensed. An order processing device receives a pharmaceutical order and identifies a size of container into which a pharmaceutical in the pharmaceutical order should be dispensed. A pallet sizing and pucking device is configured: to configure a pallet with a plurality of pucks adapted to accommodate containers and to configure the pucks on a pallet in a manner that will facilitate efficient fulfillment of the pharmaceutical order.

20 Claims, 15 Drawing Sheets

(56) References Cited

U.S. PATENT DOCUMENTS

| | | | |
|---|---|---|---|
| 7,814,734 B2 * | 10/2010 | Bilkie, Jr. | ............... B65B 55/20 |
| | | | 53/473 |
| 7,995,831 B2 | 8/2011 | Eller | |
| 8,256,813 B2 | 9/2012 | Hsieh | |
| 8,731,711 B1 | 5/2014 | Joplin | |
| 10,086,974 B2 * | 10/2018 | Joplin | .................... B65B 3/003 |
| 10,639,786 B2 * | 5/2020 | Joplin | .................... B25J 9/0093 |
| 2005/0258657 A1 | 11/2005 | Gebauer | |
| 2013/0344629 A1 | 12/2013 | Baek | |
| 2014/0023461 A1 | 1/2014 | Schaller | |
| 2014/0105717 A1 | 4/2014 | Looi | |
| 2014/0105719 A1 * | 4/2014 | Mueller | ............... B25J 15/0475 |
| | | | 414/800 |

* cited by examiner

METHODS AND SYSTEMS FOR PALLET SIZING AND PUCKING

CROSS REFERENCE TO RELATED APPLICATION

This application claims priority to and is a continuation of U.S. patent application Ser. No. 16/118,630 filed on Aug. 31, 2018; said application is a continuation of U.S. patent application Ser. No. 14/798,344 filed on Jul. 13, 2015 and issued as U.S. Pat. No. 10,086,974 on Oct. 2, 2018; the entire disclosures of which are incorporated herein by reference.

FIELD

The present application relates generally to the technical field relates to automated filling centers. In a specific example, the present application may relate to a high volume fulfillment center, e.g., a high volume pharmacy and to systems and devices used in filling prescriptions and prescription orders at a high volume pharmacy.

BACKGROUND

A high-volume pharmacy may process and fill a large number of prescriptions and prescription orders. Automated systems may be used by a high-volume pharmacy to process and fulfill prescriptions. The automated systems may include enabled transportation of empty, filled, and/or closed containers to various areas in the pharmacy.

DETAILED DESCRIPTION

Example systems and methods for pallet sizing and pucking are described. In the following description, for purposes of explanation, numerous specific details are set forth in order to provide a thorough understanding of example embodiments. It will be evident, however, to one of ordinary skill in the art that embodiments of the invention may be practiced without these specific details.

Generally, a prescription order is generated for a high volume pharmacy. The prescription order may include more than one prescription drug for fulfillment. Each prescription drug in a prescription order is an order component of the prescription order. Generally, the order components are pill bottles or other containers and packaging having a quantity of a prescription drug therein.

These containers may be transported throughout portions of the pharmacy by use of pallets containing a number of cavities. Pucks may be placed in these cavities of the pallet that are differently sized and shaped receptacles to accommodate containers of differing sizes. The arrangement of pucks in a pallet may be determined based on prescriptions or prescription orders.

Figure 1:
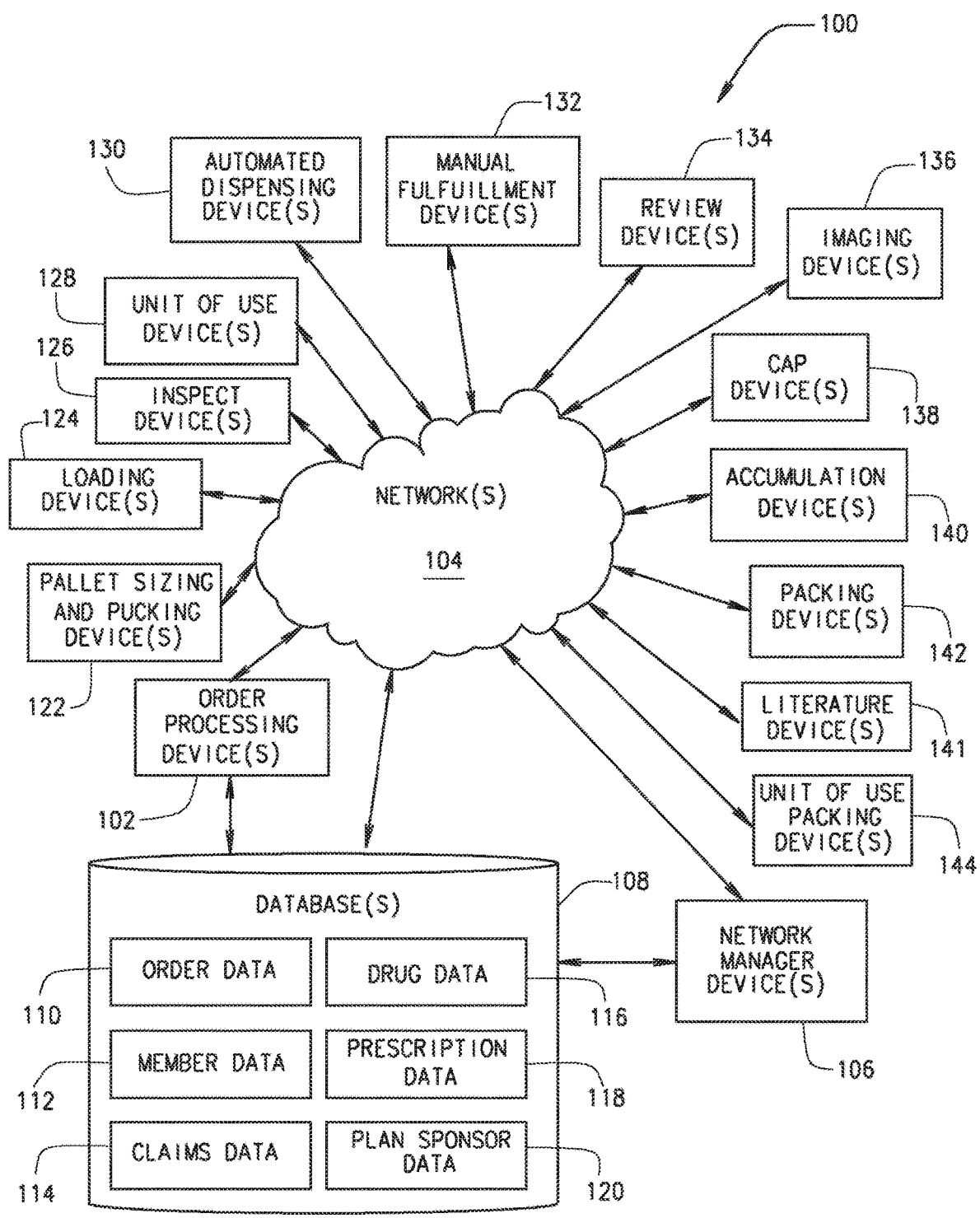
FIG. 1 is a block diagram of an example system, according to an example embodiment.

FIG. 1 is a block diagram of an example system 100, according to an example embodiment. While the system 100 is generally described as being deployed in a high volume pharmacy (e.g., a mail order pharmacy, a direct delivery pharmacy, an automated pharmacy, and the like), the system 100 may otherwise be deployed. The system 100 may include an order processing device 102 in communication with a benefit manager device 106 over a network 104. Additional devices which may be in communication with the benefit manager device 106 and/or the order processing device 102 over network 104 include: database(s) 108 which may store one or more than one of order data 110, member data 112, claims data 114, drug data 116, prescription data 118, and plan sponsor data 120; pallet sizing and pucking device(s) 122; loading device(s) 124; inspect device(s) 126; unit of use device(s) 128; automated dispensing device(s) 130; manual fulfillment device(s) 132; review device(s) 134; imaging device(s) 136; cap device(s) 138; accumulation device(s) 140; literature device(s) 141; packing device(s) 142; and unit of use packing device(s) 144. The system 100 may also include additional devices, which may communicate with each other over network 104 or directly.

The order processing device 102 may receive information about prescriptions being filled at a pharmacy in which the order processing device 102 is deployed. In general, the order processing device 102 is a device located within or otherwise associated with a pharmacy location to enable fulfillment of a prescription by dispensing prescription drugs. In some embodiments, the order processing device 102 may be a device separate from a pharmacy that enables communication with other devices located within a pharmacy. For example, the order processing device 102 may be in communication with another order processing device 102 and/or other devices 122-144 located with a pharmacy. In some embodiments, an external pharmacy order processing device 102 may have limited functionality (e.g., as operated by a patient requesting fulfillment of a prescription drug) when an internal pharmacy order processing device 102 may have greater functionality (e.g., as operated by a pharmacy).

The order processing device 102 may track a prescription order as it is fulfilled. A prescription order may include one or more than one prescription to be filled by the pharmacy. The order processing device 102 may make pharmacy routing decisions and/or order consolidation decisions for a prescription order. The pharmacy routing decisions include what device or devices in the pharmacy are responsible for filling at least a portion of the prescription order, where the order consolidation decisions include whether portions of a prescription order or multiple prescription orders should be shipped together for a patient or a patient family. The order processing device 102 may operate on its own or in combination with the benefit manager device 106. The order processing device 102 may track and/or schedule the literature or other paperwork associated with each order or multiple prescription orders that are being shipped together.

Examples of the devices 102, 106 include a set-top box (STB), a receiver card, a mobile telephone, a personal digital assistant (PDA), a display device, a portable gaming unit, a tablet, and a computing system; however other devices may also be used. For example order processing device 102 may include a mobile electronic device, such an IPHONE or IPAD device by Apple, Inc. mobile electronic devices powered by ANDROID by Google, Inc. and a BLACKBERRY device by Blackberry Limited. The devices 102, 106 may also include other computing devices, such as desktop computing devices, notebook computing devices, netbook computing devices, gaming devices, servers, and the like. The devices 102, 106 may include circuitry, a processor, a memory to store data and instructions, and communication functionality. Other types of electronic devices that can use rules and instructions to execute various functions may also be used.

Examples of the network 104 include Mobile Communications (GSM) network, a code division multiple access (CDMA) network, $3^{rd}$ Generation Partnership Project (3GPP), an Internet Protocol (IP) network, a Wireless Application Protocol (WAP) network, a WiFi network, or an IEEE 802.11 standards network, as well as various combinations thereof. The network 104 may include optical communications. The network 104 may be a local area network or a global communication network, such as the Internet. Other conventional and/or later developed wired and wireless networks may also be used. In some embodiment, the network 104 may include a prescribing network such as the electronic prescribing network operated by Surescripts of Arlington, Va.

The benefit manager device 106 is a device operated by an entity at least partially responsible for creation and/or management of the pharmacy or drug benefit. While this benefit manager operating the benefit manager device 106 is typically a pharmacy benefit manager (PBM), other entities may operate the benefit manager device 106 either on behalf of themselves, the PBM, or another entity. For example, the benefit manager may be operated by a health plan, a retail pharmacy chain, a drug wholesaler, a data analytics or other type of software-related company, or the like. In some embodiments, a PBM that provides the pharmacy benefit may also provide one or more than one additional benefits including a medical or health benefit, a dental benefit, a vision benefit, a wellness benefit, a radiology benefit, a pet care benefit, an insurance benefit, a long term care benefit, a nursing home benefit, and the like. The PBM may, in addition to its PBM operations, operate one or more than one pharmacy. The pharmacies may be retail pharmacies, mail order pharmacies, or otherwise.

Some of the operations of the PBM that operates the benefit manager device 106 may include the following. A member (or a person on behalf of the member) of a pharmacy benefit plan administered by or through the PBM attempts to obtain a prescription drug at a retail pharmacy location where the member can obtain drugs in a physical store from a pharmacist or pharmacist technician, or in some instances through mail order drug delivery from a mail order pharmacy location. The member may also obtain a prescription drug directly or indirectly through the use of a machine, such as a kiosk, vending unit, mobile electronic device, or a different type of mechanical, electrical, electronic communication device, and/or computing device.

The member may have a co-pay for the prescription drug that reflects an amount of money that the member is responsible to pay the pharmacy for the prescription drug. The money paid by the member to the pharmacy may come from the personal funds of the member, a health savings account (HSA) of the member or the member's family, a health reimbursement arrangement (HRA) of the member or the member's family, a flexible spending accounts (FSA) of the member or the member's family, or the like. An employer of the member may directly or indirectly fund or reimburse the member or an account of the member for the co-pay.

The amount of the co-pay paid by the member may vary by the benefit plan of a plan sponsor or client with the PBM. The member's co-pay may be based on a flat co-pay (e.g., $10), coinsurance (e.g., 10%), and/or a deductible (e.g., for first $500 of annual prescription drug spend) for certain prescription drugs, certain types and/or classes of prescription drugs, and/or all prescription drugs.

In certain instances, the member may not pay the co-pay or may only pay for a portion of a co-pay for a prescription drug. For example, if the usual and customary cost for a generic version of a prescription drug is $4, and the member's flat co-pay is $20 for the prescription drug, the member may only pay $4 to receive the prescription drug. In another example involving a worker's compensation claim, no co-pay may be due by the member for the prescription drug. The co-pay may also vary based on the delivery channel used to receive the prescription drug. For example, the co-pay for receiving prescription drug from a mail order pharmacy location may be less than the co-pay for receiving prescription drug from a retail pharmacy location.

In conjunction with receiving the co-pay (if any) from the member and dispensing the prescription drug to the member, the pharmacy submits a claim to the PBM for the prescription drug. The PBM may perform certain adjudication operations including verifying the eligibility of the member, reviewing an applicable formulary of the member to determine appropriate co-pay, coinsurance, and deductible for the prescription drug, and performing a drug utilization review (DUR) on the member. The PBM then provides a response to the pharmacy following performance of at least some of the aforementioned operations. As part of the adjudication, the plan sponsor (or the PBM on behalf of the plan sponsor) ultimately reimburses the pharmacy for filling the prescription drug when the prescription drug was successfully adjudicated. The aforementioned adjudication operations generally occur before the co-pay is received and the prescription drug dispensed. However, the operations may occur simultaneously, substantially simultaneously, or in a different order. In addition, more or less adjudication operations may be performed as at least part of the adjudication process.

The amount of reimbursement paid to the pharmacy by a plan sponsor and/or money paid by the member may be based at least in part on the type of pharmacy network in which the pharmacy is included. Other factors may be used to determine the amount in addition to the type of pharmacy network. For example, if the member pays the pharmacy for the prescription without using the prescription drug benefit provided by the benefit manager, the amount of money paid by the member may be higher and the amount of money received by the pharmacy for dispensing the prescription drug and for the prescription drug itself may be higher. Some or all of the foregoing operations may be performed by executing instructions on the benefit manager device 106 and/or an additional device.

In some embodiments, at least some of the functionality of the order processing device 102 may be included in the benefit manager device 106. The order processing device 102 may be in a client-server relationship with the benefit manager device 106, a peer-to peer relationship with the benefit manager device 106, or in a different type of relationship with the benefit manager device 106.

The order processing device 102 and/or the benefit manager device 106 may be in communication directly (e.g., through local storage or peer-to-peer connection(s)) and/or through the network 104 (e.g., in a cloud configuration or software-as-a-service) with a database 108 (e.g., as may be retained in memory or otherwise). The database 108 may be deployed on the order processing device 102, the benefit manager device 106, on another device of the system 100, or otherwise. The database 108 may store order data 110, member data 112, claims data 114, drug data 116, prescription data 118, and/or plan sponsor data 120. Other data may be stored in the database 108.

The order data 110 may include data related to the order of prescriptions including the type (e.g., drug name and strength) and quantity of each prescription in a prescription order. The order data 110 may also include data used for completion of the prescription, such as prescription materials and/or the type and/or size of container in which the drug is or is preferably dispensed. In general, prescription materials are a type of order materials that include an electronic copy of information regarding the prescription drug for inclusion with or otherwise in conjunction with the fulfilled prescription. The prescription materials may include electronic information regarding drug interaction warnings, recommended usage, possible side effects, expiration date, date of prescribing, or the like. The order data 110 may be used by a high volume fulfillment center to fulfill a pharmacy order.

In some embodiments, the order data 110 includes verification information associated with fulfillment of the prescription in the pharmacy. For example, the order data 110 may include videos and/or images taken of (i) the prescription drug prior to dispensing, during dispensing, and/or after dispensing, (ii) the prescription container (e.g., a prescription bottle and sealing lid) used to contain the prescription drug prior to dispensing, during dispensing, and/or after dispensing, (iii) the packaging and/or packaging materials used to ship or otherwise deliver the prescription drug prior to dispensing, during dispensing, and/or after dispensing, and/or (iv) the fulfillment process within the pharmacy. Other type of verification information such as bar code data read from pallets used to transport prescriptions within the pharmacy may also be stored as order data 110.

The member data 112 includes information regarding the members associated with the benefit manager. The information stored as member data 112 may include personal information, personal health information, protected health information, and the like. Examples of the member data 112 include name, address, telephone number, e-mail address, prescription drug history, and the like. The member data 112 may include a plan sponsor identifier that identifies the plan sponsor associated with the member and/or a member identifier that identifies the member to the plan sponsor. The member data 112 may include a member identifier that identifies the plan sponsor associated with the patient and/or a patient identifier that identifies the patient to the plan sponsor. The member data 112 may also include, by way of example, dispensation preferences such as type of label, type of cap, message preferences, language preferences, or the like.

The member data 112 may be accessed by various devices in the pharmacy, e.g., the high volume fulfillment center, to obtain information utilized for fulfillment and shipping of prescription orders. In some embodiments, an external order processing device 102 operated by or on behalf of a member may have access to at least a portion of the member data 112 for review, verification, or other purposes.

In some embodiments, the member data 112 may include information for persons who are patients of the pharmacy but are not members in a benefit plan being provided by the benefit manager. For example, these patients may obtain drug directly from the pharmacy, through a private label service offered by the pharmacy, the high volume fulfillment center, or otherwise. In general, the use of the terms member and patient may be used interchangeably herein.

The claims data 114 includes information regarding pharmacy claims adjudicated by the PBM under a drug benefit program provided by the PBM for one, or more than one, plan sponsors. In general, the claims data 114 includes an identification of the client that sponsors the drug benefit program under which the claim is made, and/or the member that purchased the prescription drug giving rise to the claim, the prescription drug that was filled by the pharmacy (e.g., the national drug code number), the dispensing date, generic indicator, GPI number, medication class, the cost of the prescription drug provided under the drug benefit program, the copay/coinsurance amount, rebate information, and/or member eligibility. Additional information may be included.

In some embodiments, other types of claims beyond prescription drug may be stored in the claims data 114. For example, medical claims, dental claims, wellness claims, or other type of health care-related claims for members may be stored as a portion of the claims data 114.

In some embodiments, the claims data 114 includes claims that identify the members with whom the claims are associated. In some embodiments, the claims data 114 includes claims that have been de-identified (e.g., associated with a unique identifier but not with a particular, identifiable member).

The drug data 116 may include drug name (e.g., technical name and/or common name), other names by which the drug is known by, active ingredients, an image of the drug (e.g., in pill form), and the like. The drug data 116 may include information associated with a single medication or multiple medications.

The prescription data 118 may include information regarding prescriptions that may be issued by prescribers on behalf of patients, who may be members of the drug benefit plan, for example to be filled by a pharmacy. Examples of the prescription data 118 include patient names, medication or treatment (such as lab tests), dosing information, and the like. The prescriptions may be electronic prescriptions, paper prescriptions that have been scanned, or otherwise. In some embodiments, the dosing information reflects a frequency of use (e.g., once a day, twice a day, before each meal, etc.) and a duration of use (e.g., a few days, a week, a few weeks, a month, etc.).

In some embodiments, the order data 110 may be linked to associated member data, claims data 114, drug data 116, and/or prescription data 118.

The plan sponsor data 120 includes information regarding the plan sponsors of the benefit manager. Examples of the plan sponsor data 120 include company name, company address, contact name, contact telephone number, contact e-mail address, and the like.

The order processing device 102 may direct at least some of the operations of the devices 122-144, recited above. In some embodiments, operations performed by one of these devices 122-144 may be performed sequentially, or in parallel with the operations of another device as may be coordinated by the order processing device 102. In some embodiments, the order processing device 102 tracks a prescription with the pharmacy based on operations performed by one or more of the devices 122-144.

In some embodiments, the system 100 may transport prescription drug containers (e.g., between one or more than one of the devices 122-144 in the high volume fulfillment center) by use of pallets. The pallet sizing and pucking device 122 may configure pucks in a pallet. A pallet may be a transport structure for a number of prescription containers, and may include a number of cavities. A puck may be placed in one or more than one of the cavities in a pallet by the pallet sizing and pucking device 122. A puck may include a receptacle sized and shaped to receive a prescription container. Such containers may be supported by the pucks during carriage in the pallet and during movement through the fulfillment process. Different pucks may have differently sized and shaped receptacles to accommodate containers of differing sizes, as may be appropriate for different prescriptions. Pucks allow the standardization of equipment engaging differently sized drug containers such that some automated equipment can move the drug container by gripping the puck that is supporting the container and allow the use of a standardized pallet that holds a plurality of pucks have a same outer dimension while having differently sized receptacles therein to hold differently sized drug containers. The pucks may also operate to ensure that a drug container is centered in a location on the pallet.

The arrangement of pucks in a pallet may be determined by the order processing device 102 based on prescriptions which the order processing device 102 decides to launch. In general, prescription orders in the order database 110 reside in one or more than one queues, and are generally launched in a first-in-first-out order. However, the order processing device 102 may use logic and a variety of factors to determine when and how prescriptions are to be launched. For example, some non-limiting factors which may alter the first-in-first-out order of launching prescriptions in a pharmacy include the age of the order, whether the order required an outreach to a physician or some other intervention, whether there are any performance guarantees with plan sponsors or members, the available inventory of a given pharmaceutical in view of existing prescriptions already launched which will require that pharmaceutical, the zip code to which the order will be shipped, the workload and volume of various parts of the pharmacy, whether valid paperwork for the order has been received, and/or similar orders for the same pharmaceutical that are already to be launched. The logic may be implemented directly in the pallet sizing and pucking device 122, in the order processing device 102, in both devices 102, 122, or otherwise. Once a prescription is set to be launched, a puck suitable for the appropriate size of container for that prescription may be positioned in a pallet by a robotic arm or pickers. The pallet sizing and pucking device 122 may launch a pallet once pucks have been configured in the pallet.

The loading device 124 may load prescription containers into the pucks on a pallet by a robotic aim, a pick and place mechanism, or the like. In one embodiment, the loading device 108 has robotic arms or pickers to grasp a prescription container and move it to and from a pallet. The loading device 124 may also print a label which is appropriate for a container that is to be loaded onto the pallet, and apply the label to the container. The pallet may be located on a conveyor assembly during these operations. In an example, the drug containers may be positioned in the pucks by the loading device 124 prior to the pucks being placed in the pallet.

The inspect device 126 may verify that containers in a pallet are correctly labeled and in the correct spot on the pallet. The inspect device 126 may scan the label on one or more than one container on the pallet. Labels of containers may be scanned or imaged in full or in part by the inspect device 126. Such imaging may occur after the container has been lifted out of its puck by a robotic arm, picker, or the like, or may be otherwise scanned or imaged while retained in the puck. In some embodiments, images and/or video captured by the inspect device 126 may be stored in the database 108 as order data 110.

The unit of use device 128 may temporarily store, monitor, label and/or dispense unit of use products. In general, unit of use products are prescription drug products that may be delivered to a patient or member without being repackaged at the pharmacy. These products may include pills in a container, pills in a blister pack, inhalers, and the like. Prescription drug products dispensed by the unit of use device 128 may be packaged individually or collectively for shipping, or may be shipped in combination with other prescription drugs dispensed by other devices in the high volume fulfillment center.

The automated dispensing device 130 may include one or more than one devices that dispense prescription drugs or pharmaceuticals into prescription containers in accordance with one or multiple prescription orders. In general, the automated dispensing device 130 may include mechanical and electronic components with, in some embodiments, software and/or logic to facilitate pharmaceutical dispensing that would otherwise be performed in a manual fashion by a pharmacist and/or pharmacist technician. For example, the automated dispensing device 130 may include high volume fillers that fill a number of prescription drug types at a rapid rate and blister pack machines that dispense and pack drugs into a blister pack. Prescription drugs dispensed by the automated dispensing devices 130 may be packaged individually or collectively for shipping, or may be shipped in combination with other prescription drugs dispenses by other devices in the high volume fulfillment center.

The manual fulfillment device 132 may provide for manual fulfillment of prescriptions. For example, the manual fulfillment device 132 may receive or obtain a container and enable fulfillment of the container by a pharmacist or pharmacy technician. In some embodiments, the manual fulfillment device 132 provides the filled container to another device in the system 100. In an example embodiment, the container may be joined with other containers in a prescription order for a patient or member, e.g., on a pallet or at the accumulation device 140. In general, a manual fulfillment may include operations at least partially performed by a pharmacist or pharmacy technician. For example, a person may retrieve a supply of the prescribed drug, may make an observation, may count out a prescribed quantity of drugs and place them into a prescription container, or the like. Some portions of the manual fulfillment process may be automated by use of a machine. For example, counting of capsules, tablets, or pills may be at least partially automated (e.g., through use of a pill counter). Prescription drugs dispensed by the manual fulfillment device 132 may be packaged individually or collectively for shipping, or may be shipped in combination with other prescription drugs dispenses by other devices in the high volume fulfillment center.

The review device 134 may process prescription containers to be reviewed by a pharmacist for proper pill count, exception handling, prescription verification, and the like. Fulfilled prescriptions may be manually reviewed and/or verified by a pharmacist, as may be required by state or local law. A pharmacist or other licensed pharmacy person who may dispense certain drugs in compliance with local and/or other laws may operate the review device 134 and visually inspect a prescription container that has been filled with a prescription drug. The pharmacist may review, verify, and/or evaluate drug quantity, drug strength, and/or drug interaction concerns, or otherwise perform pharmacist services. The pharmacist may also handle containers which have been flagged as an exception, such as containers with unreadable labels, containers for which the associated prescription order has been cancelled, containers with defects, and the like. In an example embodiment, the manual review can be performed at the manual station.

The imaging device 136 may image containers once they have been filled with pharmaceuticals. The imaging device 136 may measure the fill height of the pharmaceuticals in the container based on the obtained image to determine if the container is filled to the correct height given the type of pharmaceutical and the number of pills in the prescription. Images of the pills in the container may also be obtained to detect the size of the pills themselves and markings thereon. The images may be transmitted to the order processing device 102, and/or stored in the database 110 as part of the order data 110.

The cap device 138 may be used to cap or otherwise seal a prescription container. In some embodiments, the cap device 138 may secure a prescription container with a type of cap in accordance with a patient preference (e.g., a preference regarding child resistance), a plan sponsor preference, a prescriber preference, or the like. The cap device 138 may also etch a message into the cap or otherwise associate a message into the cap, although this process may be performed by a subsequent device in the high volume fulfillment center.

The accumulation device 140 accumulates various containers of prescription drugs in a prescription order. The accumulation device 140 may accumulate prescription containers from various devices or areas of the pharmacy. For example, the accumulation device 140 may accumulate prescription containers from the unit of use device 128, the automated dispensing device 130, the manual fulfillment device 132, and the review device 134, at the high volume fulfillment center. The accumulation device 140 may be used to group the prescription containers prior to shipment to the member or otherwise.

In some embodiments, the literature device 141 folds or otherwise prepares the literature for inclusion with a prescription drug order (e.g., in a shipping container). In some embodiments, the literature device 141 that prints the literature may be separate from the literature device that prepares the literature for inclusion with a prescription order.

The packing device 142 packages a prescription order in preparation for shipping the order. The packing device 142 may box, bag, or otherwise package the fulfilled prescription order for delivery. The packing device 142 may further place inserts, e.g., literature or other papers, into the packaging received from the literature device 141 or otherwise. For example, bulk prescription orders may be shipped in a box, while other prescription orders may be shipped in a bag which may be a wrap seal bag. The packing device 142 may label the box or bag with the address and a recipient's name. The label may be printed and affixed to the bag or box, be printed directly onto the bag or box, or otherwise associated with the bag or box. The packing device 142 may sort the box or bag for mailing in an efficient manner (e.g., sort by delivery address). The packing device 142 may include ice or temperature sensitive elements for prescriptions which are to be kept within a temperature range during shipping in order to retain efficacy or otherwise. The ultimate package may then be shipped through postal mail, through a mail order delivery service that ships via group and/or air (e.g., UPS, FEDEX, or DHL), through delivery service, through a local delivery service (e.g., a courier service), through a locker box at a shipping site (e.g., an AMAZON locker or a post office box), or otherwise.

The unit of use packing device 144 packages a unit of use prescription order in preparation for shipping the order. The unit of use packing device 144 may include manual scanning of containers to be bagged for shipping to verify each container in the order. In an example embodiment, the manual scanning may be performed at a manual station.

While the system 100 in FIG. 1 is shown to include single devices 102, 106, 122-144 multiple devices may be used. The devices 102, 106, 122-144 may be the same type or model of device or may be different device types or models. When multiple devices are present, the multiple devices may be of the same device type or models or may be a different device type or model. The types of devices 102, 106, 122-144 shown in FIG. 1 are example devices. In other configurations of the system 100, lesser, additional, or different types of devices may be included. Moreover, the system 100 shows a single network 104; however, multiple networks can be used. The multiple networks may communicate in series with each other to link the devices 102, 106, 122-144 or in parallel to link the devices 102, 106, 122-144. Multiple devices may share processing and/or memory resources. The devices 102, 106, 122-144 may be located in the same area or in different locations. For example, the devices 102, 106, 122-144 may be located in a building or set of adjoining buildings. The devices 102, 106, 122-144 may be interconnected (e.g., by conveyors), networked, and/or otherwise in contact with one another or integrated with one another, e.g., at the high volume fulfillment center. In addition, the functionality of a device may be split among a number of discrete devices and/or combined with other devices.

The system 100 may include a single database, or multiple databases, maintained by respective devices operated by or on behalf one or a number of different persons and/or organizations. The communication may occur directly (e.g., through local storage) and/or through the network 104 (e.g., in a cloud configuration or software-as-a-service) with a device that stores a respective database. FIG. 1 represents an example deployment of the database 108. However, the system 100 is not limited to this configuration. The database 108 may be deployed separately from and/or one or more than one of the devices 102, 106, 122-144, partially on more than one of the devices 102, 106, 122-144, or may otherwise be deployed. The deployment may occur on local storage, remote storage, removable storage, and/or a different type of storage associated with the devices 102, 106, 122-144. Additionally, while a single database is generally depicted, multiple databases may be implemented. In the case of multiple databases, the different databases may be deployed on different systems, including the devices 102, 106, 122-144 and/or a third-party device or network.

Figure 2:
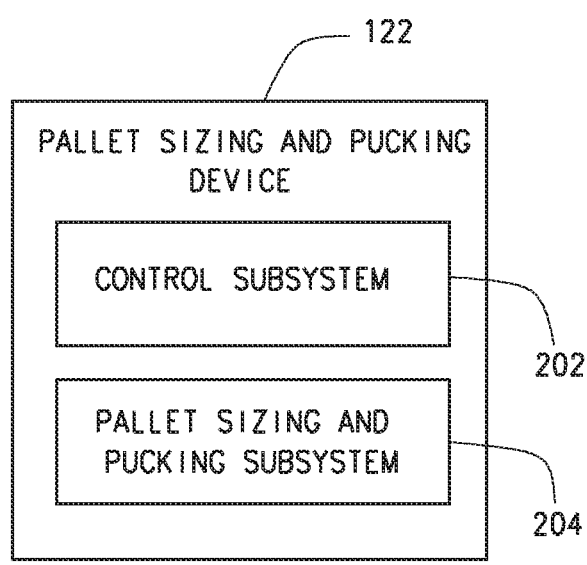
FIG. 2 is a block diagram of an example pallet sizing and pucking device that may be deployed within the system of FIG. 1, according to an example embodiment.
Figure 3:
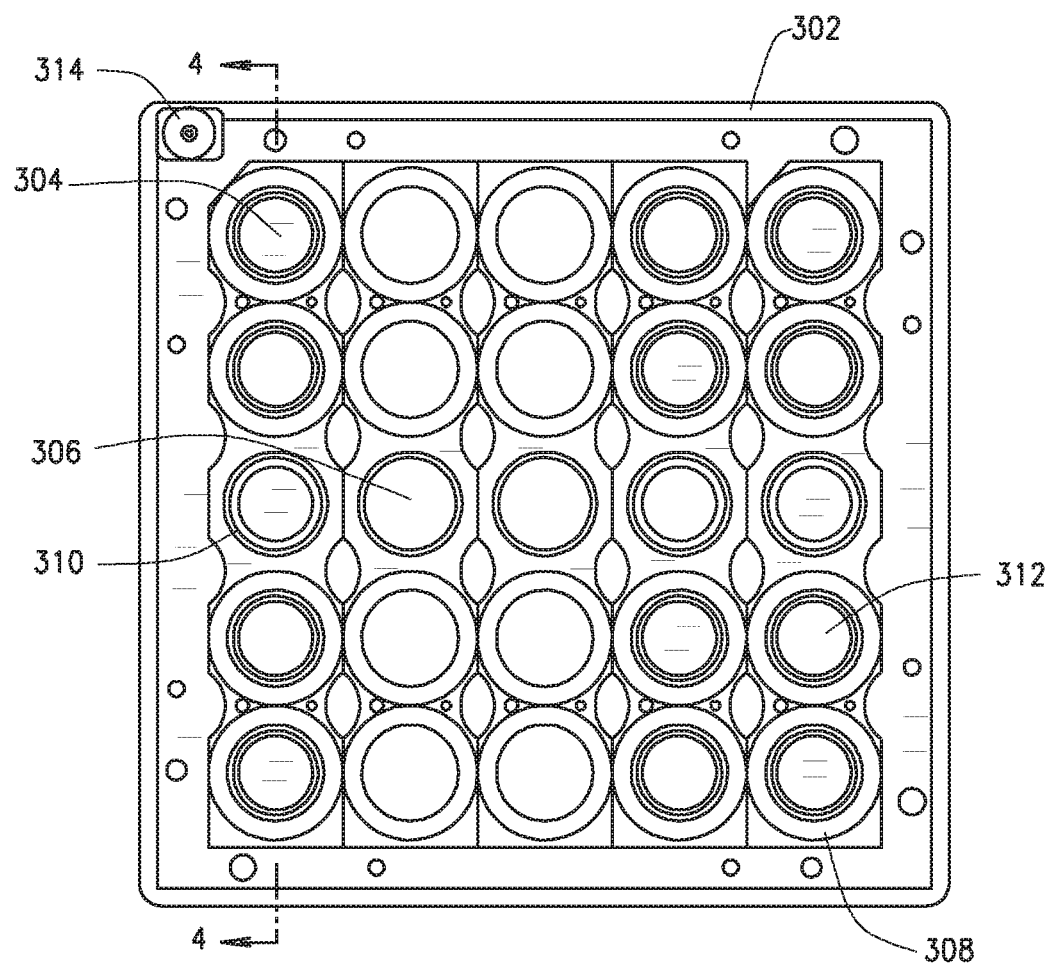
FIG. 3 is a top view of a pallet that includes containers and pucks that may be deployed within the system of FIG. 1, according to an example embodiment.
Figure 4:
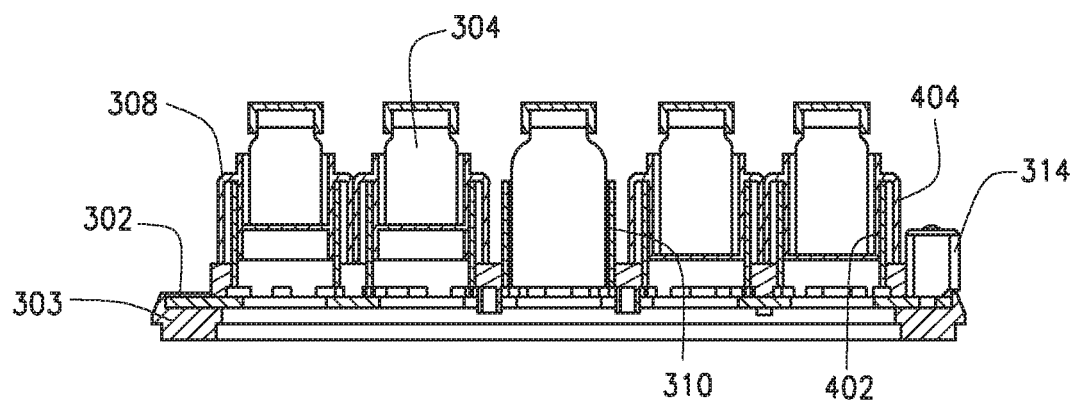
FIG. 4 is a cross sectional view of the pallet of FIG. 3, at line 4 of FIG. 3, according to an example embodiment.

FIG. 2 illustrates the pallet sizing and pucking device 122, according to an example embodiment. The pallet sizing and pucking device 122 may be deployed in the system 100 of FIG. 1, or may otherwise be used. The pallet sizing and pucking device 122 may include a control subsystem 202 and a pallet sizing and pucking subsystem 204. The control subsystem 202 may include one or more module and enables the pallet sizing and pucking device 122 to control the pallet sizing and pucking subsystem 204, while the pallet sizing and pucking subsystem 204 may include one or more devices and enables the pallet sizing and pucking device 122 with pallet sizing and pucking operations (e.g., configuring pucks in a pallet).

FIGS. 3-6 illustrate a pallet 302, according to an example embodiment. The pallet 302 may be used in the system 100 of FIG. 1 (e.g., by the pallet sizing and pucking device 122), or may be otherwise used.

The pallet 302 may be a transport structure for a number of prescription containers 304, and may include a number of cavities 306. While the pallet 302 is shown to include 25 cavities in a five by five cavity row/column configuration, other numbers of categories and/or cavity configurations of varying shapes, size, and/or dimensions may be used. In some embodiments the pallet may be substantially square and, in such an embodiment, have a width and length of between approximately 18 inches and 22 inches (e.g., approximately 18 inches, 19 inches, 20 inches, 21 inches, or 22 inches). In some embodiments, the width and/or length may be greater than approximately 22 inches or less than approximately 18 inches.

In an example embodiment, the cavities 306 are be spaced on the pallet 302 such that the center point of adjacent cavities 306 is between approximately 3 inches and 4 inches (e.g., approximately 3 inches, 3.25 inches, 3.5 inches, 3.75 inches or 4 inches). In another example embodiment, the distance between center points of adjacent cavities 306 is more than approximately 4 inches. In yet another example embodiment, the center points of cavities 306 are less than approximately 3 inches apart.

In an example embodiment, the pallet 302 includes a base 303. The base 303 may be formed from multiple components or as a single component. The height of the base 303 may be approximately 1 inch. In other example embodiments, the combined height of the base 303 and puck nests is less than approximately 1 inch or greater than approximately 1 inch. The base 303 may be made in whole or in part of metal, such as aluminum. Other suitable materials may be used for base 303, such as plastic. The pallet 302 may include bumpers.

In some embodiments, other carriers beyond the pallet 302 and/or no carrier may be used to move containers or groups of containers through the system 100 or via the pallet sizing and pucking subsystem 204.

The pallet 302 may retain one or more than one containers 304. A container 304 is generally cylindrical and may be of one or a variety of sizes utilized by a pharmacy for fulfillment of a prescription. For example, a pharmacy may have two different sized containers or three different sized containers. Any number of different sized containers may be used with the pallet 302. The containers 304 may be selected (e.g., by a pharmacist, by a device in the pharmacy such as the pallet sizing and pucking device 122, or otherwise) based on container size availability, filling considerations of the container 304, cost of the container 304, the size and/or quantity of pharmaceuticals to be placed within the container 304, dimensions of the container 304, shipping considerations (e.g., cost to ship the prescription drug to a patient) associated with delivery of the container 304, drug handling considerations, or otherwise. While the container 304 is generally denoted as being used with the pallet 302, the containers 304 may otherwise be used in the system 100 or in a different system. Shapes beyond cylindrical shapes may be used for the containers 304. Examples of other shapes include regular prisms, elliptical cylinders, and combinations thereof. The receptacle of a puck may be sized to receive and support the outer shape of the container.

An example configuration of container usage with a pharmacy includes a small container 304 having a volume of approximately 75 cc, a medium container 304 having a volume of approximately 120 cc, and a large container 304 having a volume of approximately 200 cc. An example configuration of container usage with a pharmacy includes a small container 304 having a volume of 110 cc and a large container 304 having a volume of approximately 165 cc.

Figure 5:
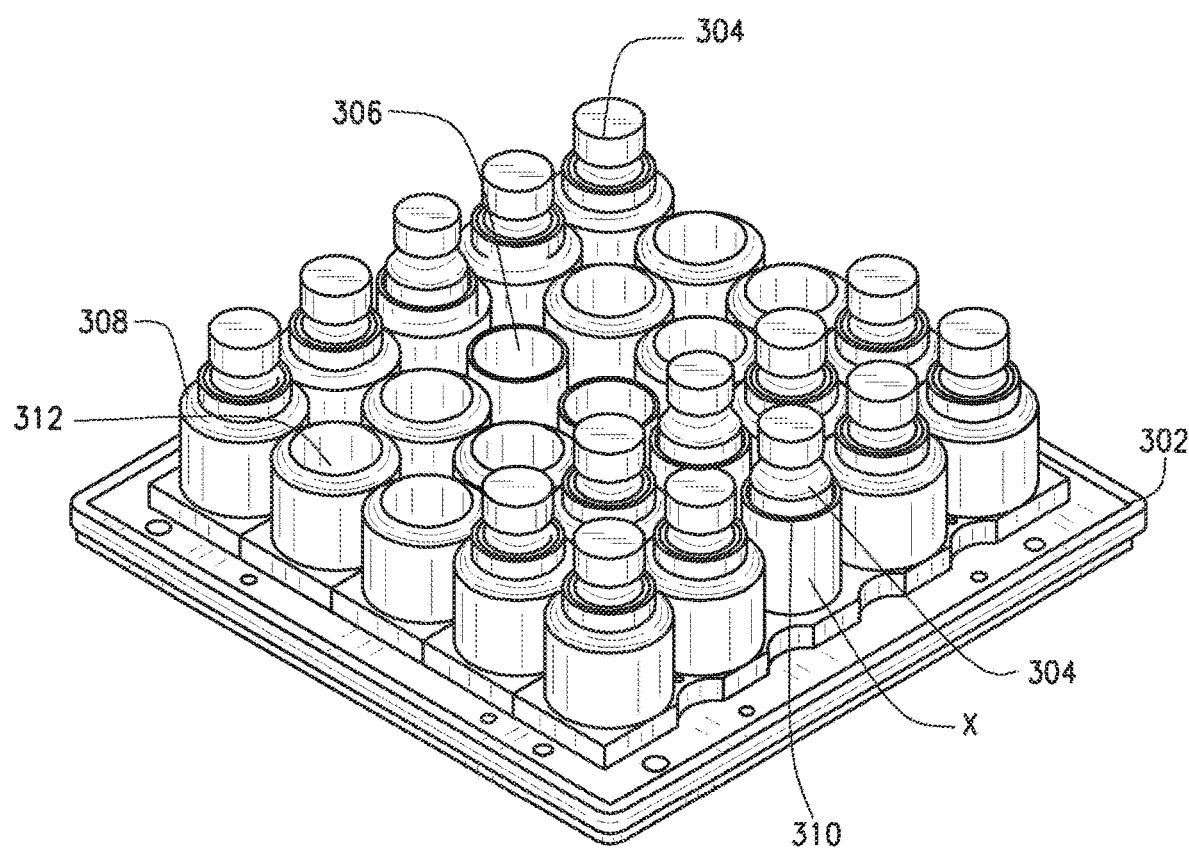
FIG. 5 is a perspective view of the pallet of FIG. 3, according to an example embodiment.
Figure 6:
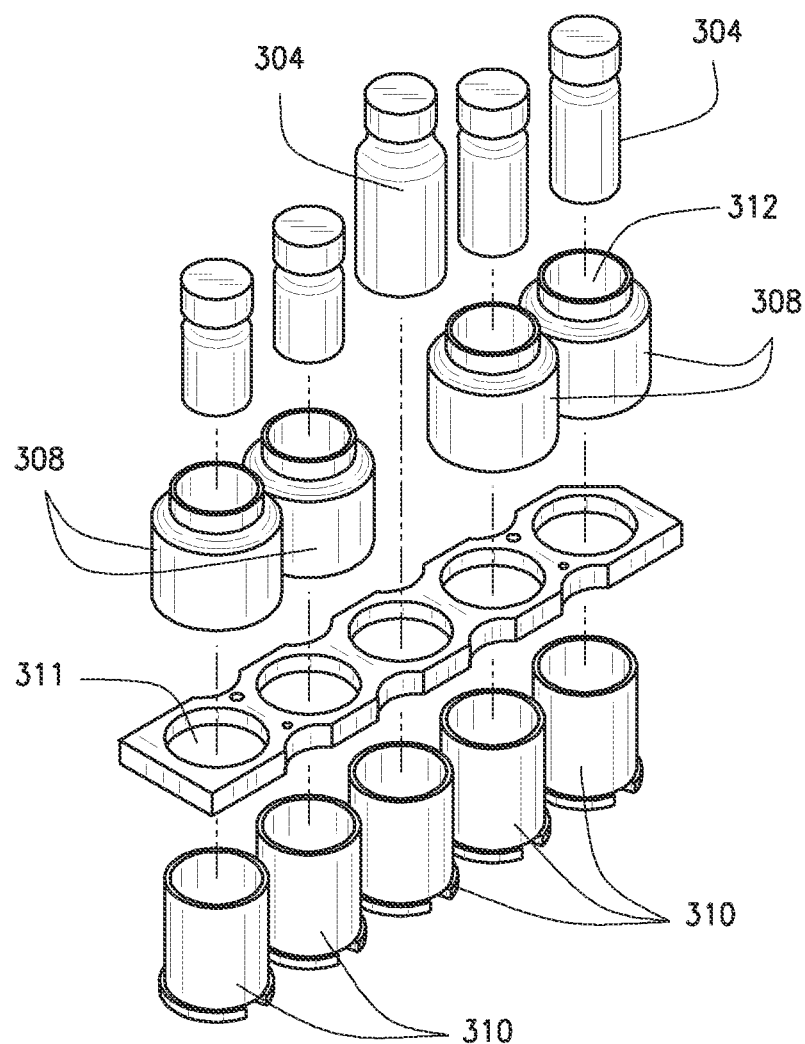
FIG. 6 is an exploded view of a portion of the pallet of FIG. 3, according to an example embodiment.

According to an example embodiment, inserts 310 may be placed through holes 311 of the pallet 302 to form the cavities 306. The inserts 310 may be adapted to hold a large container 304 in a generally secure manner. For example, an internal diameter of the insert 310 may be slightly larger than an external diameter of the container 304. FIG. 5, at position X, illustrates a large container 304 disposed within an insert 310 of the pallet 302, according to an example embodiment. In an example embodiment, the insert 310 has an internal diameter of approximately 2.3 inches and is adapted to receive a 220 cc container 304 with an external diameter of between approximately 2.2 inches and 2.3 inches, such that the difference between such diameters is between approximately 0.05 inches and approximately 0.1 inches. In another example embodiment, the difference between such diameters is less than 0.05 inches or more than approximately 0.1 inches. The insert 310 may have an external diameter of approximately 2.7 inches and a height of approximately 2.7 inches. Other sizes of inserts 310 maybe used in other embodiments.

The inserts 310 may be formed of polymer, plastic, metal, or other suitable materials. In an example embodiment, the inserts 310 are plastic or polymer.

A puck 308 may be adapted to fit over an insert 310 of the pallet 302. The puck 308 may include a receptacle 312 to accommodate a container 304 with a particular size or shape. For example, the insert 310 may fit between an interior wall 402 and an exterior wall 404 of a puck 308.

In some embodiments, the pucks 308 may be shaped and configured differently to enable retaining containers 304 of different sizes within an approximately same sized cavity 306 throughout the pallet 302. The use of pucks 308 enables different sized containers 304 to be retained with the pallet 302 at an approximately uniform height and in an approximate uniform relative position throughout at least a portion of the pallet 302. For example, the pucks 308 may be adapted to both permit medium and small containers 304, respectively, to be held with relative security in a cavity 306 (e.g., by effectively narrowing the diameter of the cavity 306) and to position the tops of all containers 304 within the pallet 302 at a substantially uniform height (e.g., by effectively raising or lowering the bottom of the cavity 306). In some embodiments, the pucks 308 may also include pucks generally adapted to hold a large container. Through such a configuration, the pallet may be configured and reconfigured to maintain different size containers in a manner that enables devices in a pharmacy to generally be agnostic to the container dimensions in a particular position on the pallet 302.

The receptacle 312 of the puck 308 may adapted to hold a medium container 304 with relative security. For example, the inner diameter of the puck 308 may be between approximately 2 inches and 2.1 inches, the outer diameter of the medium container may be approximately 2 inches, and the difference between such diameters may be between approximately 0.05 inches and approximately 0.1 inches. In other example embodiments, the difference between such diameters is less than 0.05 inches or more than approximately 0.1 inches.

The puck 308 may be adapted to hold a small container 304 with relative security and, when the puck 308 is inserted over the insert 310 of the pallet 302, the cavity 306 is then adapted to hold a small container 304 with relative security.

In an example embodiment, a container 304 is held within the pallet 302 with relative security when the container 304 will not move relative to the pallet 302 as the pallet 302 moves throughout a pharmacy unless the container 304 itself is moved by machine or hand.

The pallet 302 may include a radio-frequency identification (RFID) tag 314. The RFID tag 314 may be an active RFID tag, such as an active RFID tag with a close reading range. In some embodiments, the RFID tag 314 is an active, narrowband, read/write RFID tag.

The RFID tag 314 of a particular pallet 302 may store data (or otherwise facilitate the access of data, e.g., from the database 108) associated with the containers 304 that have been, are, and/or will be placed within the pallet 302, such as the order data 110, the member data 112, the claims data 114, the drug data 116, the prescription data 118, and/or the plan sponsor data 120 associated with such containers 304. Other data may be stored by and/or or associated with the RFID tag 314, such as the age of the pallet 302, the number of times the pallet 302 has been used to transport containers 304 through the system 100, the number of errors associated with the pallet 302, and the like. The RFID tag 314 may also store the position of individual containers on the pallet. In an example embodiment, the RFID tag 314 of the pallet 302, while deployed within a pallet sizing and pucking subsystem 204, stores data associated with one or more of the following data fields: (1) pallet identifier, (2) container identifier, (3) container properties, (4) pallet route, (5) group status (e.g., status of a group of containers), (6) number of 75 cc pucks on a pallet, and (7) number of 120 cc pucks on a pallet.

Figure 7:
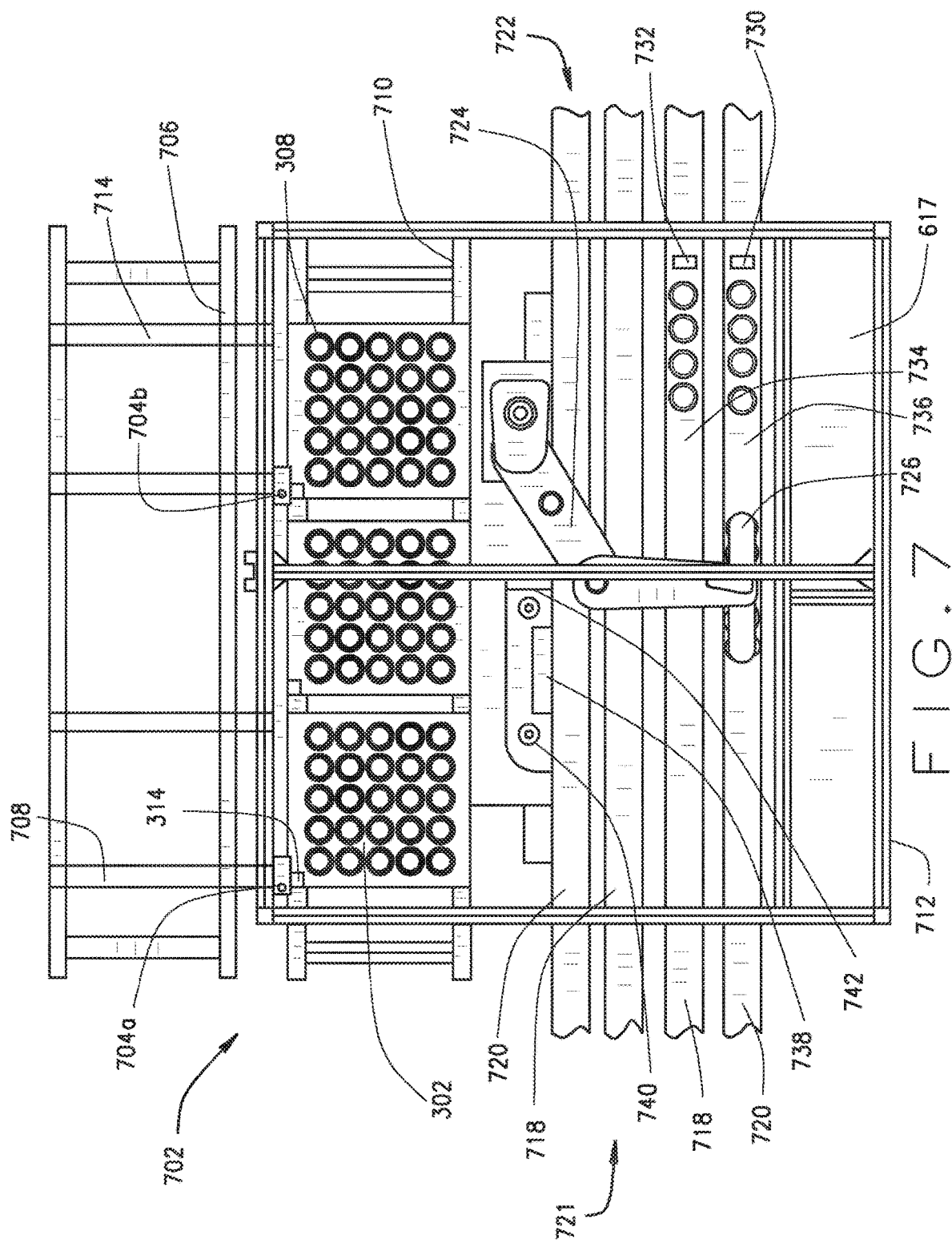
FIG. 7 is a top view of a pucking station, according to an example embodiment, according to an example embodiment.
Figure 8:
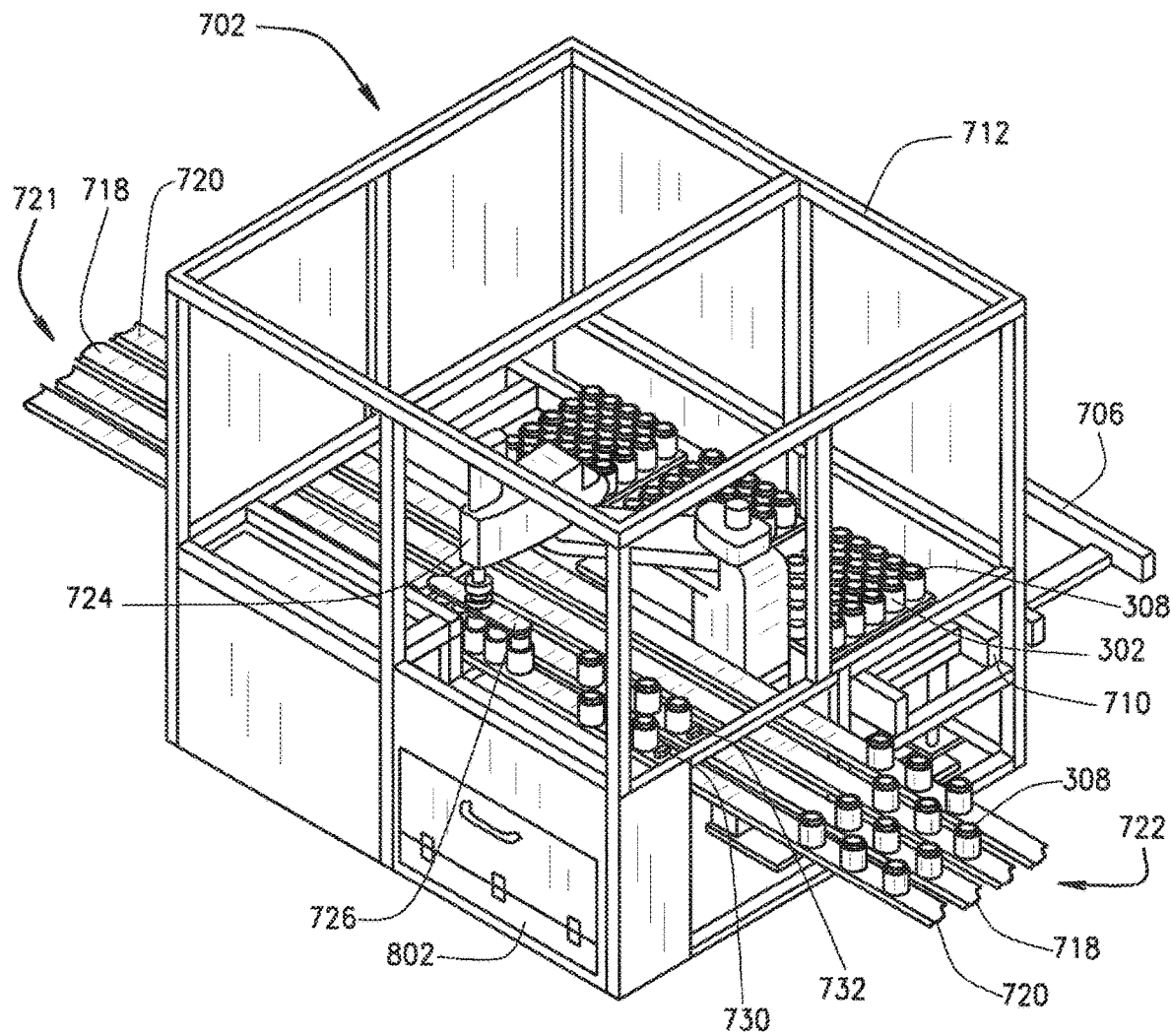
FIG. 8 is a perspective view of the pucking station of FIG. 7, according to an example embodiment.
Figure 9:
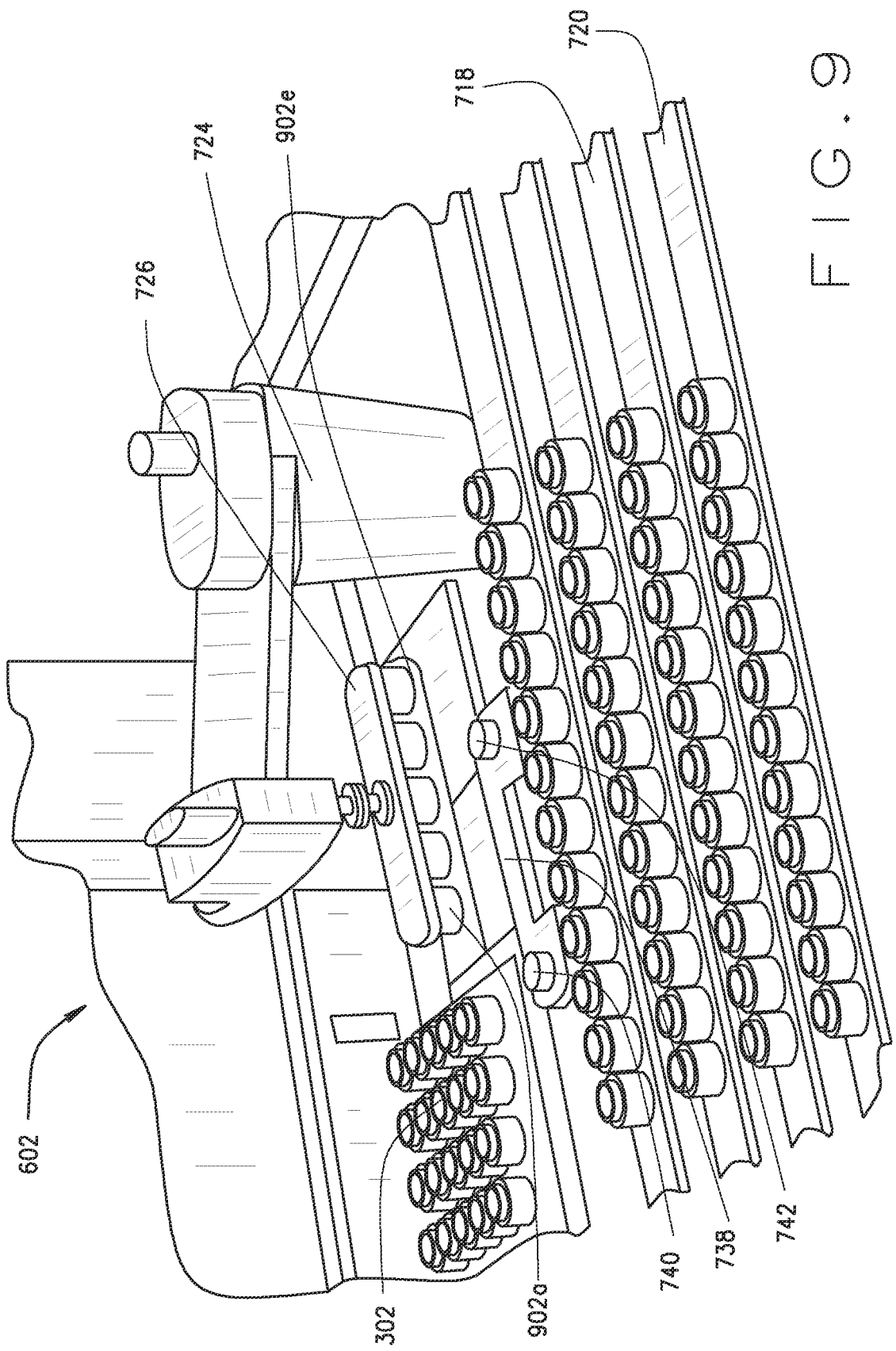
FIG. 9 is a partial, perspective view of the pucking station of FIG. 7, according to an example embodiment.

FIGS. 7-9 illustrate a pucking station 702 according to an example embodiment. The pucking station 702 may perform pallet sizing and pucking operations of the pallet sizing and pucking subsystem 204, including one or more than one of the operations of loading the pucks 308 onto the pallets 302, unloading the pucks 308 from the pallets 302, and sorting the pucks 308 to be loaded onto the pallets 302 or that have been unloaded from the pallets 302. The pallet sizing and pucking operations of the pallet sizing and pucking subsystem 204 may be performed to configure the pallet 302 with the pucks 308 so that it can receive empty containers for filling and/or receive filled containers for receiving dispensed pharmaceuticals, capping and/or other purposes, such as order consolidation, distribution within the system 100, and preparation for shipment, among other reasons. Other operations may be performed by the pucking station 702.

The pucking station 702 may include pucking station RFID readers 704a, 704b. The pucking station RFID reader 704a may be an in-bound RFID reader (e.g., an RFID reader that reads the RFID tag 314 of the pallet 302 as it enters the pucking station 702) and the pucking station RFID reader 704b may be an out-bound RFID reader (e.g., an RFID reader that reads the RFID tag 314 of the pallet 302 as it exits the pucking station 702). Other types or configurations of RFID readers may be used in other embodiments. Although two pucking station RFID readers 704a, 704b are illustrated in the embodiment of FIG. 7, in other embodiments, the pucking station 302 includes only one pucking station RFID reader. In yet other embodiments, the pucking station 302 includes more than two pucking station RFID readers. The number of pucking station RFID readers that may be included in the pucking station 302 may be determined based on cost of the pucking station RFID readers, functionality of the pucking station RFID readers, a desire of where to monitor the RFID tag 314 of the pallet 302 while within the pucking station 302, or otherwise.

The pucking station RFID readers 704a, 704b may read data on the RFID tag 314 of the pallet 302 to obtain data associated with the particular pallet 302, such as such as the order data 110, the member data 112, the claims data 114, the drug data 116, the prescription data 118, and/or the plan sponsor data 120. The pucking station RFID readers 704a, 704b may write data to the RFTD tag 314 of the pallet 302 (or otherwise cause data to be associated with the pallet 302), such as the order data 110, the member data 112, the claims data 114, the drug data 116, the prescription data 118, and/or the plan sponsor data 120 associated with new orders (or portions thereof) to be filled by the system 100 using one or more than one containers 304 that will be placed in the pallet 302.

In some embodiments, the pucking station RFID reader 704a and/or the pucking station RFID reader 704b reads the following information from the RFID tag 314 of the pallet 302 when it enters the pucking station 702: the pallet identifier, the number of 75 cc pucks on the pallet 302, and the number of 120 cc pucks on the pallet 302. The pucking station RFID reader 704a and/or the pucking station RFID reader 704b may erase all contents of the RFID tag 314, other than the pallet identifier, the number of 75 cc pucks on the pallet, and the number of 120 cc pucks on the pallet. The pucking station RFID 704a and/or the pucking station RFID reader 704b reader may write the following data to the RFID tag 314: (1) container identifier, (2) container properties, (3) pallet route, (4) group status (i.e., status of a group of containers), (5) number of 75 cc pucks on the pallet 302, and (6) number of 120 cc pucks on the pallet 302.

A system conveyor 706 may transport the pallets 302 through some or all of the devices 124-144 within the system 100, such as the pallet sizing and pucking device 122.

As illustrated in FIG. 7, an in-bound lift and transfer unit 708 may divert or otherwise move the pallet 302 from the system conveyor 706 onto a pallet conveyor 710 that delivers the pallets 302 through a frame portion 712 of the pucking station 702. An out-bound lift and transfer unit 714 may move the pallet 302 from the pallet conveyor 710 onto the system conveyor 706.

Although separate in-bound and out-bound lift and transfer units 708, 714 are illustrated in an embodiment shown in FIG. 7, in other embodiments either or both of the lift and transfer units 708, 714 may operate to both move pallets from the system conveyor 706 to the pallet conveyor 710 and from the pallet conveyor 710 to the system conveyor 706. Furthermore, although two lift and transfer units are illustrated in FIG. 7, fewer or more than two lift and transfer units 708, 714 may be deployed in other embodiments of the pucking station 702. The in-bound lift and transfer unit 708 may be adapted to stop the pallet 302 when the pucking station 702 is not full and transfer the pallet 302 into the pucking station 702 and, when the pucking station 702 is full, to allow the pallet 302 to pass the pucking station 702, e.g., to go on to another pucking station 702, as described below.

Somewhat similarly, the out-bound lift and transfer unit 714 may be adapted to stop the pallet 302 if the configuration of the pallet 302 with pucks 308 has been completed at the pucking station 702 and move the pallet 302 from the pallet conveyor 710 to the system conveyor 706. Alternatively, if the configuration of the pallet 302 with pucks 308 is incomplete, the out-bound lift and transfer unit 714 may allow the pallet 302 to pass through the pucking station 702, e.g., to go into another pucking station 702, as described below.

The system conveyor 706 and/or the pallet conveyor 710 may be a chain conveyor or a belt conveyer, e.g., a Bosch TS2 belt-driven conveyor; other types of conveyors may be used for the system conveyor 706 and/or the pallet conveyor 710, such as a chain conveyor. In some embodiments, the system conveyor 706 and/or the pallet conveyor 710 is a low friction, high speed conveyor.

The pallet 302 may be retained in a fixed position within the pucking station 702 while the pucks 308 are loaded onto or removed from the pallet 302. The pallet conveyor 710 may continue to move under the pallet 302 while it is held in a fixed position.

The puck conveyors 718, 720 may circulate within the pallet sizing and pucking subsystem 204 to deliver the pucks 308 to and from the pucking station 702. Thus the pucking station 702 may include portions of the puck conveyors 718, 720 that, in operation, move in one direction (e.g., toward a first end 721 of the pucking station 702) and portions that move in another directions (e.g., toward a second end 722 of the pucking station 702). The puck conveyors 718, 720 may be chain conveyors or belt conveyors, e.g., Bosch VarioFlow chain conveyors, such as the Bosch VarioFlow chain conveyor model number VF90.

The frame portion 712 supports a robot arm 724 within the pucking station 702, as well as portions of the pallet conveyor 710 and the puck conveyors 718, 720 disposed within the frame portions 712. The robot arm 724 may be a low weight bearing, high speed, high accuracy assembly-type robot arm. In a particular embodiment, the robot arm 724 is a selective compliance assembly robot arm ("SCARA"), such as a SCARA robot from Adept Technology, Inc. Low weight may refer to less than ten pounds, less than five pounds, less than two pounds or less than one pound. Low weight may refer to at least the weight of a heaviest puck used in the system 100. Other types of robot arms may be used for the robot arm 724. The robot arm 724 may perform operations such as removing the pucks 308 from the pallet 302 and placing the pucks 308 onto the pallet 302. Other operations may be performed by the robot arm 724. In some embodiments, operations of removing the pucks 308 from the pallet 302 or placing the pucks 308 onto the pallet 302 may be performed without the use of the robot arm.

The robot arm 724 may be adapted to grip the pucks 308. The pucks 308 may be lifted and moved by the robot arm 724 from the pallets 302, released, and placed onto the puck conveyors 718, 720, such as a portion of the puck conveyors 718, 720 adapted to move toward a first end 721 of the pucking station 702. The robot arm 724 may be adapted to selectively release a first set of pucks 308 (e.g., a set of pucks adapted to receive a small container) onto one of the puck conveyors 718, 720 (e.g., puck conveyor 718) and a second set of pucks 308 (e.g., a set of pucks adapted to receive a medium container) onto another of the puck conveyors 718, 720 (e.g., puck conveyor 720), thereby sorting the pucks 308 removed from the pallet 302 by size. The robot arm 724 may be adapted to selectively remove a first set of pucks 308 (e.g., a set of pucks adapted to receive a small container) from the pallet 302 and place the pucks 308 onto one of the puck conveyors 718, 720 (e.g., puck conveyor 718) and to selectively remove a second set of pucks 308 (e.g., a set of pucks adapted to receive a medium container) onto another puck conveyors 718, 720 (e.g., puck conveyor 720) thereby sorting the pucks 308 removed from the pallet 302 by size. The pucks may further be sorted according other characteristics of the puck.

The robot arm 724 includes a gripper assembly 726. The gripper assembly 726 includes gripper heads 902a, 902e, shown as five gripper heads in FIG. 9. The gripper heads 902a, 902e may be adapted to grip the pucks 308 while on the pallet 302 and may be further adapted to grip the pucks 308 while on the puck conveyors 718, 720, thereby enabling the robot arm 724 to remove the pucks 308 from the pallet 302 and/or from the puck conveyors 718, 720. The gripper heads 902a, 902e may be further adapted to release the pucks 308, thereby enabling the robot arm 724 to place the pucks 308 onto the puck conveyors 718, 720 and/or onto the pallet 302. The gripper heads 902a, 902e may be independently actuated, pneumatic gripper heads. In an example embodiment, the gripper heads 902a, 902e are spring assist closed. In another an example embodiment, the gripper heads 902a, 902e are spring assist open. While five gripper heads are shown in FIG. 9 including the gripper heads 902a, 902e, the gripper assembly 726 may include a greater or lesser number of gripper heads. In some embodiments, the number of gripper heads included in the gripper assembly matches the number of cavities 306 in a row or column of the pallet 302.

A stop unit 730, 732 may hold the pucks 308 within a portion of the puck conveyors 718, 720 to form a puck holding area 734, 736 within the puck conveyors 718, 720 (such as a portion of the puck conveyors 718, 720 adapted to move toward a second end 722 of the pucking station 702). The stop unit 730, 732 may be further adapted to open, thereby releasing the pucks 308 from the puck holding area 734, 736 such that the pucks 308 can circulate within and through the pallet sizing and pucking subsystem 204. Operations of the stop unit 730, 732 may be controlled by the control subsystem 202 or otherwise.

The pucks 308 in the puck holding areas 734, 736 may be gripped, lifted, and moved by the robot arm 724 from the puck holding areas 734, 736 to the pallet 302 being held within the pucking station 702 and placed into the cavities 306 of the pallet 302.

In an example embodiment, the pucks 308 adapted to hold one size of container 304 (e.g., a small container) circulate on a first puck conveyor 718 and another type of pucks 308 adapted to hold another size of container 304 (e.g., a medium container) circulate on a second puck conveyors 720. Differing puck to puck conveyor configurations may be used. For example, the pucks 308 circulating on a first puck conveyor 718 may be of a different color (e.g., to indicate different drug types, different timing considerations, or the like) than the pucks 308 circulating on a second puck conveyor 720. A puck overflow bin 802 may be adapted to receive excess pucks from puck conveyors 718, 720.

An alignment element 738 may be adapted to align the gripper assembly 726 such that the gripper assembly 726 remains aligned with (e.g., parallel to) the puck conveyors 718, 720 and with the positions (e.g., cavities 306) of the pallet 302. The alignment element 738 may include cups 740, 742 adapted to fit within the gripper heads 902a, 902e. When the gripper heads 902a, 902e are disposed onto cups 740, 742, the gripper assembly 726 may align with the positions (e.g., cavities 306) of the pallet 302 and with the puck conveyors 718, 720. The control subsystem 202 may control operations of the robot arm 724 such that the gripper assembly 726 is aligned by the alignment element 738 periodically, such as each hour, every two hours, daily, or at another interval or intervals. The gripper assembly 726 may be aligned by the alignment element 738 upon a signal generated by an operator request. Operations of the robot arm 724 may be otherwise controlled.

Figure 10:
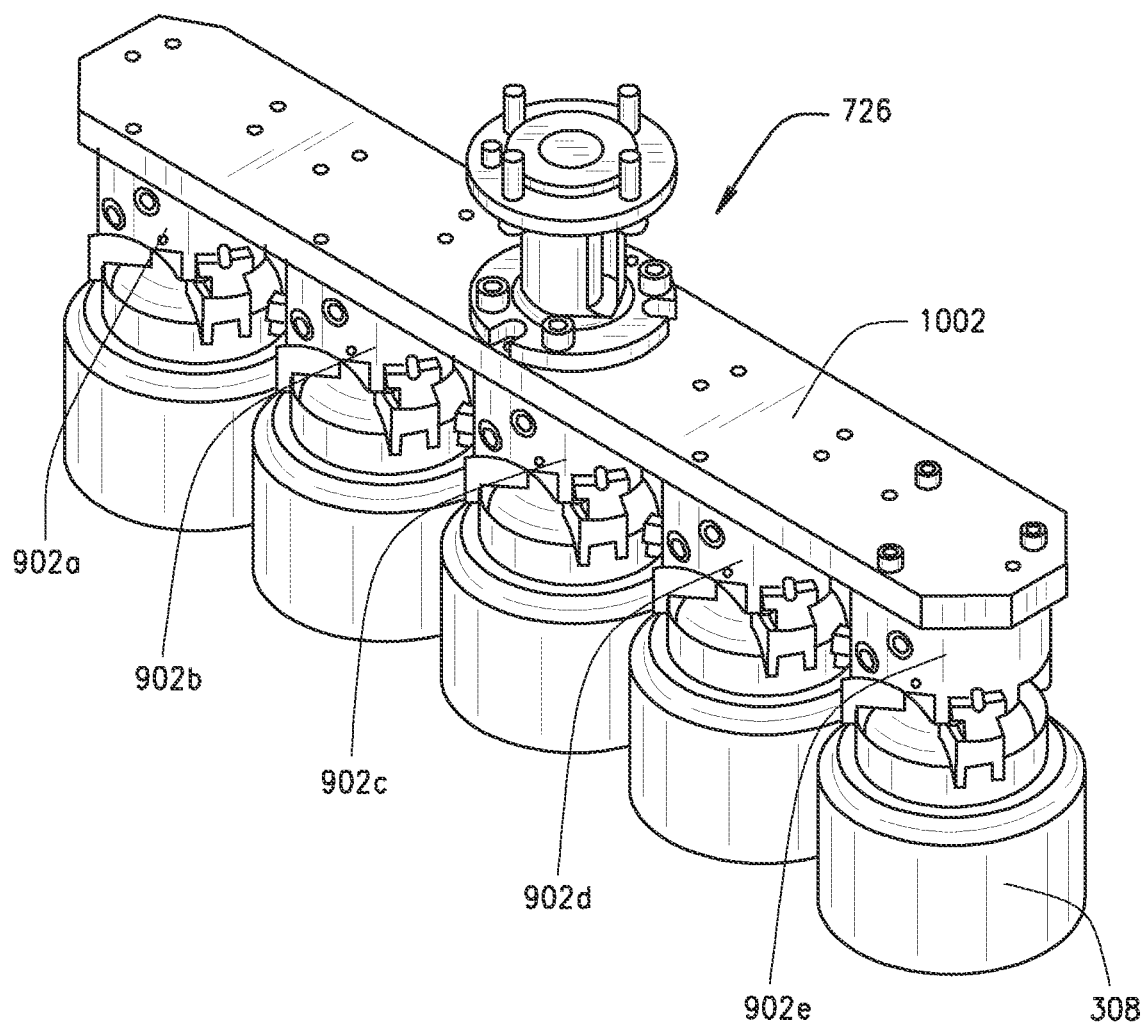
FIG. 10 is a perspective view of a gripper head that may be deployed within the pucking station of FIG. 7, according to an example embodiment.

FIG. 10 illustrates a gripper assembly 726 according to an example embodiment. The gripper assembly 726 may be deployed in a pucking station 702 or may be otherwise deployed. The gripper assembly 726 includes five gripper heads 902a, 902b, 902c, 902d, 902e. The gripper heads 902a, 902b, 902c, 902d, 902e are secured to a mounting plate 1002. As illustrated in FIG. 10, the gripper heads 902a, 902b, 902c, 902d, 902e are engaging pucks 308. In an example embodiment, the gripper heads 902a, 902b, 902c, 902d, 902e are Series GRT parallel pneumatic 3-jaw grippers with a 40 mm bore sold by PHD, Inc. Other grippers may be used for the gripper heads 902a, 902b, 902c, 902d, 902e.

The gripper assembly 726 may be configured to align with a row or column of the pallet 302. For example the number of gripper heads 902a, 902b, 902c, 902d, 902e may equal the number of positions (e.g., the cavities 306) on a row or column of the pallet 302 and may be spaced and sized to facilitate association of each gripper head 902a, 902b, 902c, 902d, 902e with a particular position (e.g., the cavity 306) on the pallet. In some embodiments, the number of gripper heads 902a, 902b, 902c, 902d, 902e may be more or less than the number of positions on a row or column of the pallet 302. Independently actuated gripper heads 902a, 902b, 902c, 902d, 902e may be configured, for example, to enable each gripper head 902a, 902b, 902c, 902d, 902e to remove a puck 308 from a position (e.g., the cavity 306), on the pallet 302 independently of whether other gripper heads 902a, 902b, 902c, 902d, 902e of the gripper assembly 726 are removing pucks 308 from the pallet positions associated with such gripper heads 902a, 902b, 902c, 902d, 902e. Thus, during a particular operation, a gripper assembly 726 with five gripper heads 902a, 902b, 902c, 902d, 902e may remove zero, one, two, three, four, or five pucks from a particular row or column of a pallet. The pucks 308 selected for removal may be in any configuration, e.g., a single puck at any position or two or more pucks adjacent to and/or spaced apart from one another.

Independently actuated gripper heads 902a, 902b, 902c, 902d, 902e may be configured, for example, to enable each gripper head 902a, 902b, 902c, 902d, 902e to select a puck 308 from a puck holding area 734, 736 on a puck conveyor 718, 720, independently of whether other gripper heads 902a, 902b, 902c, 902d, 902c of the gripper assembly 726 are selecting the pucks 308 from the puck holding areas 734, 736. Thus, during a particular operation, the gripper assembly 726 with five gripper heads 902a, 902b, 902c, 902d, 902e may select zero, one, two, three, four, or five pucks from one puck holding area (e.g., the puck holding area 734 or the puck holding area 736). Additional pucks may be selected from another puck holding area (e.g., the puck holding area 734 or the puck holding area 736). The pucks 308 may be selected from one puck holding area 734, 736 and placed onto the pallet 302 and then selected from a second puck holding area 734, 736 and placed onto the pallet 302. In some embodiments, the pucks 308 may be selected from one puck holding area 734, 736 and then another puck holding area 734, 736, and then the pucks 308 selected from both holding areas 734, 736 may be place over the inserts 310 on the pallet 302. The pucks 308 may be selected from only one holding area 734, 736. The pucks 308 selected from the puck holding area 734, 736 may be in any configuration, e.g., a single puck 308 at any position or two or more pucks 308 adjacent to and/or spaced apart from one another.

Figure 11:
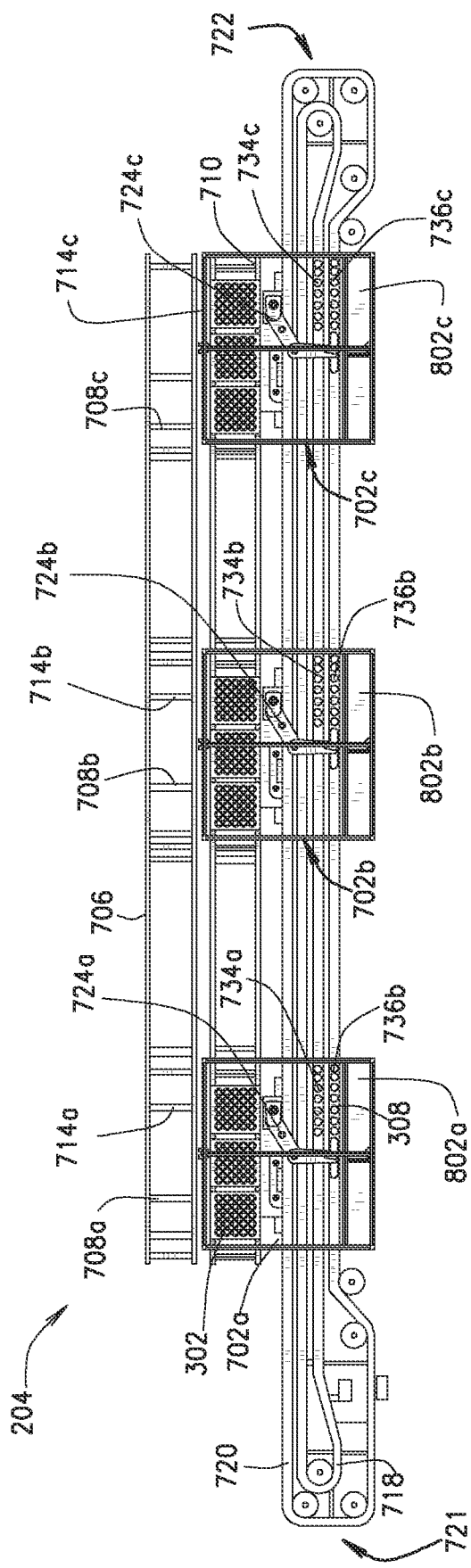
FIG. 11 is top view of a pallet sizing and pucking subsystem that may be deployed within the pallet sizing and pucking device of FIG. 2, according to an example embodiment.
Figure 12:
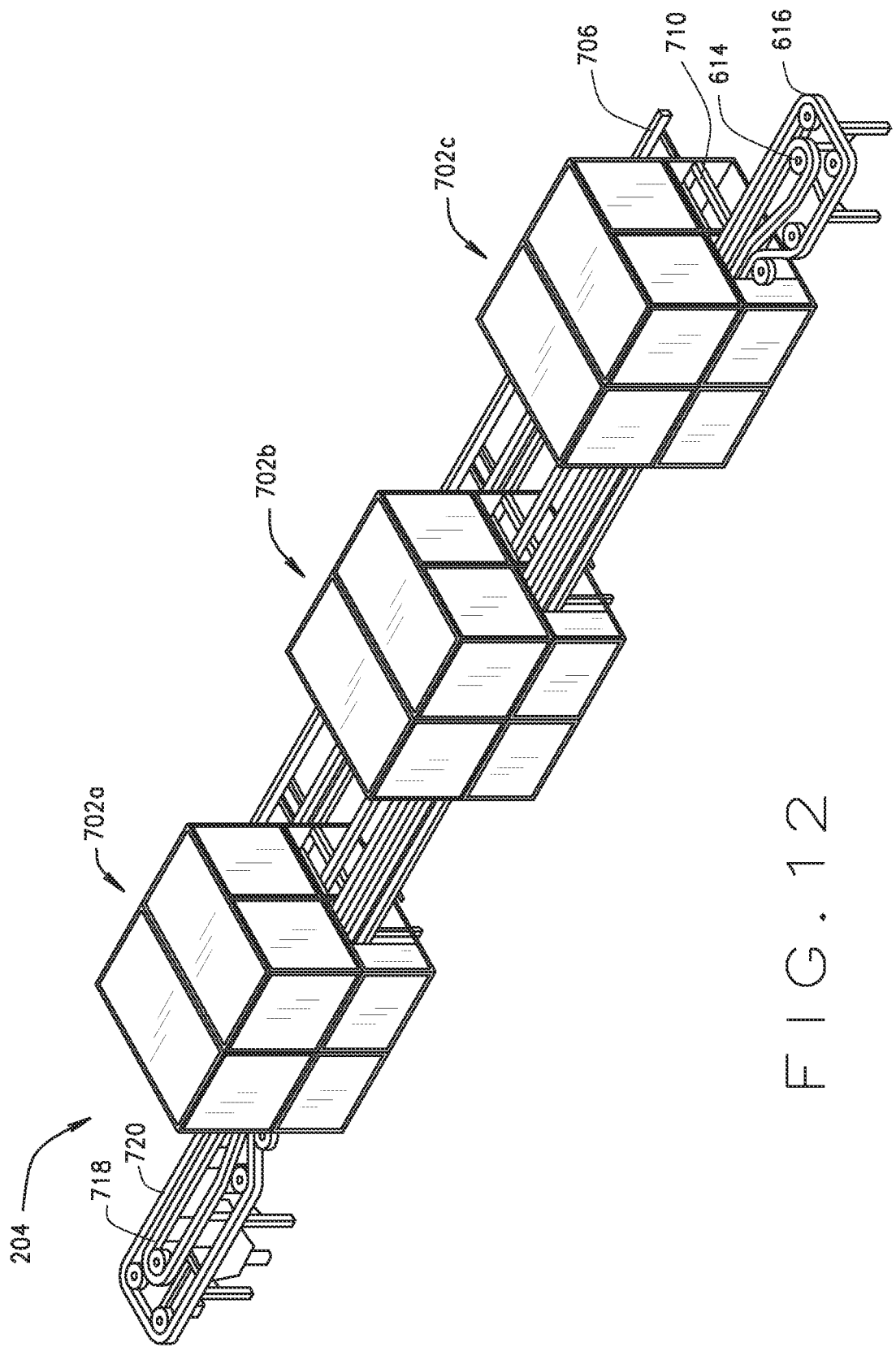
FIG. 12 is a perspective view of the pallet sizing and pucking subsystem of FIG. 11, according to an example embodiment.

FIGS. 11 and 12 illustrate the pallet sizing and pucking subsystem 204 according to an example embodiment. The pallet sizing and pucking subsystem 204 as shown includes three pucking stations 702a, 702b, 702c. However, a greater or lesser number of pucking stations 702 may be deployed in other embodiments of the pallet sizing and pucking subsystem 204.

The pucking station 702 may be employed as the pucking stations 702a, 702b, 702c of the pallet sizing and pucking subsystem 204. The pucking stations 702a, 702b, 702c, may be configurations of the pucking station 702 that include the features and functions of the pucking station 702. In other embodiments, one or more features or components of the pucking station 702 may be omitted from the pucking stations 702a, 702b, 702c and/or one or more of the pucking stations 702a, 702b, 702c may include additional features and/or components. Although three pucking stations 702a, 702b, 702c are shown in the embodiment of the pallet sizing and pucking subsystem 204, in other embodiments, the pallet sizing and pucking subsystem 204 includes less than three or more than three pucking stations 702a, 702b, 702c. In an example embodiment, the pallet sizing and pucking subsystem 204 has one pucking station 702.

In some embodiments, certain functions of the pallet sizing and pucking subsystem 204 may performed by fewer than all, including only one of, the pucking stations 702a, 702b, 702c. In an example of such an embodiment, one of the pucking stations 702a, 702b, 702c may unload pucks 308, another one of the pucking stations 702a, 702b, 702c may load pucks 308, and yet another one of the pucking stations 702a, 702b, 702c may load and unload pucks 308. In another example embodiment, pucks 308 adapted for small containers 304 are loaded and/or unloaded at one of the pucking stations 702a, 702b, 702c and pucks 308 adapted for medium containers 304 are loaded and/or unloaded at the others of the pucking stations 702a, 702b, 702c. Functions of the pallet sizing and pucking subsystem 204 may be otherwise allocated among the pucking stations 702a, 702b, 702c.

The puck conveyors 718, 720 may circulate the pucks 308 from and through the pucking stations 702a, 702b, 702c of the pallet sizing and pucking subsystem 204 and/or transport the pucks 308 to a puck overflow bin 802a, 802b, 802c. The puck conveyors 718, 720 may circulate such that some portions move in one direction (e.g., toward the first end 721) and some portions move in another direction (e.g., toward the second end 722).

Although two puck conveyors 718, 720 of the pallet sizing and pucking subsystem 204 are illustrated in FIGS. 11 and 12, more or less than two puck conveyors 718, 720 may be used. For example, a single puck conveyor may be used to transport multiple sizes of pucks 308 or additional puck conveyors may be used to transport additional (e.g., more than two) sizes of pucks 308 or to move larger quantities of pucks 308 within the pallet sizing and pucking subsystem 204 or the pucking station 702.

In-bound and out-bound lift and transfer units 708a, 708b, 708c, 714a, 714b, 714c may operate to both move pallets 302 from the system conveyor 706 to a portion of the pallet conveyor 710 disposed within a particular pucking station 702a, 702b, 702c and from the pallet conveyor 710 (e.g., a portion of the pallet conveyor 710 disposed within the pucking station 702a, 702b, 702c) to the system conveyor 706. The pucking stations 702a, 702b, 702c may each be deployed to configure pucks 308 within a particular pallet 302 and/or one or more of the pucking stations 702a, 702b, 702c may be deployed to cooperatively configure pucks 308 within a particular pallet 302.

For example, the in-bound lift and transfer unit 708a may move a particular pallet 302 to a portion of the pallet conveyor 710 disposed within the pucking station 702a, the pallet 302 may be configured by the pucking station 702a (e.g., by removing pucks 308 from and/or adding pucks 308 to the pallet), and the pallet 302 may be moved from a portion of the pallet conveyor 710 disposed within the pucking station 702a by the out-bound lift and transfer unit 714a to the system conveyor 706, which may then transport the pallet 302 to and/or move the pallet 302 within the system 100, such as to or within the loading device 124, the inspect device 126, the unit of use device 128, the automated dispensing device 130, the manual fulfillment device 132, the review device 134, the imaging device 136, the cap device 138, the accumulation device 140, and/or one or more other devices within the system 100. The pucking stations 702b, 702c may be similarly deployed and may be deployed to configure a pallet 302 disposed within that pucking station 702b, 702c while another pallet 302 disposed within another pucking station (e.g., the pucking station 702a) is being configured.

In another example, one of the in-bound lift and transfer units (e.g., the lift and transfer unit 708a or 708b) may move a particular pallet 302 to a portion of the pallet conveyor 710 disposed within one of the pucking stations (e.g., pucking station 702a or 702b), the pallet 302 may be partially configured by that pucking station 702a, 702b (e.g., by removing pucks 308 from and/or adding pucks 308 to the pallet 302), the pallet 302 may be moved by the pallet conveyor 710 into one or more of the other pucking stations (e.g., the pucking station 702b and/or 702c), the pallet 302 may be further configured by one or more of the other pucking stations 702b, 702c, and the pallet 302 may be moved from a portion of the pallet conveyor 710 disposed within one of the other pucking stations 702b, 702c by the out-bound lift and transfer unit 714b, 714c to the system conveyor 706, which may then transport the pallet 302 to and/or move the pallet 302 within the system 100.

After the pallet 302 has been used, e.g., in the system 100 to facilitate fulfillment of one or more prescriptions (e.g., a first set of prescriptions), the robot arms 724a, 724b, 724c may remove the pucks 308 from pallets 302 retained within the pucking stations 702a, 702b, 702c and place the pucks 308 on the puck conveyors 718, 720. As the pallet 302 is ready to be used, e.g., in the system to facilitate fulfillment of one or more prescriptions (e.g., a second set of prescriptions), the robot arms 724a, 724b, 724c may remove the pucks 308 from puck holding areas 734a, 734b, 734c, 736a, 736b, 736c and place them onto the pallets 302 retained within the pucking stations 702a, 702b, 702c.

Figure 13:
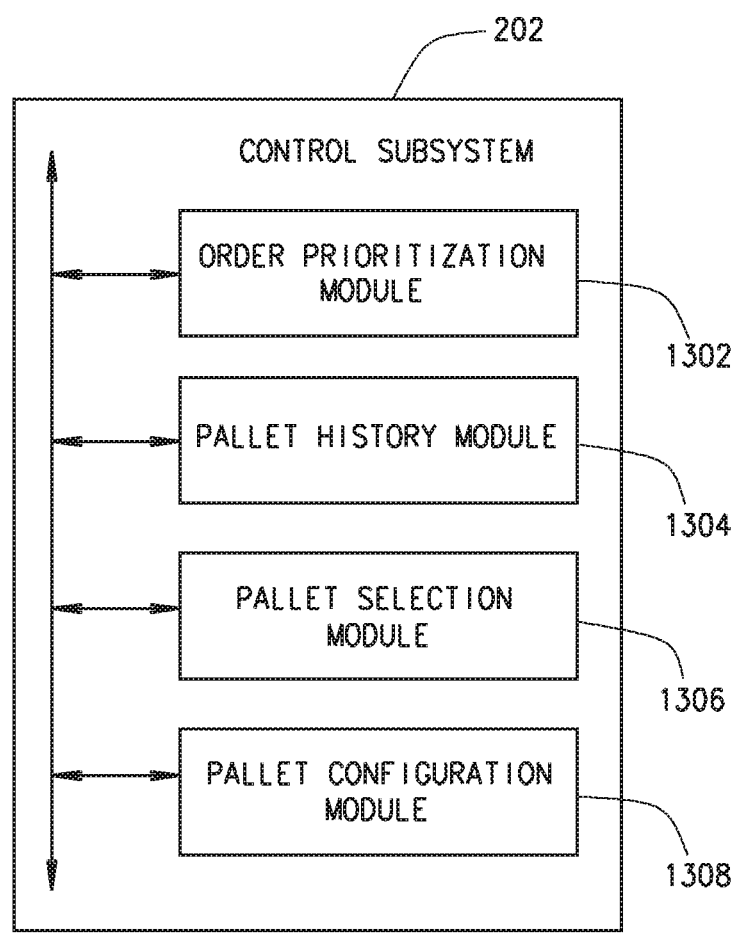
FIG. 13 is a block diagram of an example control subsystem that may be deployed in the pallet sizing and pucking device of FIG. 3, according to an example embodiment.

FIG. 13 illustrates an example control subsystem 202 that may be deployed in the order processing device 102, the pallet sizing and pucking device 122, or otherwise deployed in the system 100. One or more modules are communicatively coupled and included in the control subsystem 202 to enable control of the pallet sizing and pucking operations of the pallet sizing and pucking device 122. The modules of the control subsystem 202 that may be included are an order prioritization module 1302, the pallet history module 1304, the pallet selection module 1306, and the pallet configuration module 1308. Other modules may also be included.

In some embodiments, the modules of the control subsystem 202 may be distributed so that some of the modules are deployed in order processing device 102 and some modules are deployed in the pallet sizing and pucking device 122. In one embodiment, the modules are deployed in memory and executed by a processor coupled to the memory. The functionality of the modules may be executed in circuitry implementing instructions or in computing systems. The functionality contained within modules 1302-1308 may be combined into a lesser number of modules, further divided among a greater number of modules, or redistributed among existing modules. Other configurations including the functionality of modules 1302-1308 may be used. A module may include hardware, software and combinations thereof.

The order prioritization module 1302 may select orders (or portions of orders) to be filled using the pallets 302 to transport the containers 304 (e.g., through one or more than one of the devices 122-142 of the system 100). Orders may be selected by the order prioritization module 1302 based on factors such as the order in which the prescription was received in the pharmacy relative to other prescriptions, the age of the order (e.g., how long the prescription has been in the pharmacy), whether the order and/or the prescription required an outreach to a physician, an intervention or outreach to the patient, or otherwise, whether there are any performance guarantees with plan sponsors or members, the available inventory of a given pharmaceutical in view of existing prescriptions already launched which will utilized that pharmaceutical, the zip code to which the order will be shipped, the workload and volume of various parts of the pharmacy, whether valid paperwork for the order has been received, similar orders for the same pharmaceutical that are already to be launched, and the like. The factors may be weighted the same or differently. Other factors may be employed in selection of orders or portions of orders by the order prioritization module 1302.

The pallet history module 1304 may accesses data, such as the order data 110, the member data 112, the claims data 114, the drug data 116, the prescription data 118, and/or the plan sponsor data 120, associated with a particular pallet 302, as such pallet 302 has been deployed in the system 100 for a particular period of time or set of tasks. For example, data associated with a particular pallet 302 may be limited to data associated with a single run through the system 100. Data may be accessed from the RFID tag 314 of the pallet 302 and/or from the database 108, for example. Based on such data, the pallet history module 1304 may identify the pallet 302 as having been associated with filling errors (such as errors associated with misplacement or misalignment of containers) and, based on such identification, may control operations of the pallet sizing and pucking subsystem 204 and/or other devices within the system 100 to, for example, cause the pallet 302 to be removed through the inspect device 126 or otherwise, or otherwise generate an alert to trigger an inspection of the pallet 302. The pallet history module 1304 may identify the pallet 302 as having circulated through one or more devices (e.g., one or more than one of devices 122-142) in the system 100 a pre-determined number of times (e.g., 50 times, 100 times, 150 times, or 200 times) and, based on such identification may cause maintenance procedures to be applied to the pallet 302, such as application of an air blast or other cleaning procedures. The pallet history module 1304 may identify the configuration of the pallet, including the number of pucks 308 of each size on the pallet 302, as it enters a pucking station 702a, 702b, 702c.

The pallet selection module 1306 may determine which order or orders (or portion or portions thereof) in the queue will be filled using a particular pallet 302 to transport containers (e.g., through one or more than one of the devices 122-142). The pallet selection module 1306 may cause the pucking station RFID reader 704a, 704b to write data to the RFID tag 314 of the pallet 302. The pallet selection module 1306 may also determine to which particular pucking station 702a, 702b, 702c within the pallet sizing and pucking subsystem 204 the pallet 302 will be transported and may control operations of the pallet sizing and pucking subsystem 204 to cause the in-bound lift and transfer device 708a, 708b, 708c to transport the pallet 302 into a particular pucking station 702a, 702b, 702c. The pallet history module 1304 may determine that the pallet 302 will bypass the pallet sizing and pucking subsystem 204 and/or determine route of the pallet 302 through the system 100 (e.g., through one or more than one of the devices 122-142).

The pallet selection module 1306 may select orders (or portions of orders) based on prioritization of orders as determined by the order prioritization module 1302, based on the order history associated with the pallet 302, e.g., as identified by the pallet history module 1304, and/or may be otherwise selected. For example, orders (or portions of orders) may be selected by the pallet selection module 1306 based on one or more than one of: (1) a determination that the container requirements for such orders will be the same as or similar to the container requirements of the orders (or portions thereof) most recently filled using such the pallet 302 (e.g., that such orders will utilize the same or similar numbers of small, medium, and large containers); (2) a determination that the container requirements for such orders will be the same as or similar to the container requirements of orders (or portions thereof) likely to be subsequently filled using such pallet 302 (e.g., that such orders will require the same or similar numbers of small, medium, and large containers); (3) availability of container sizes and/or pucks 308 to adapt such container sizes to the cavities 306 of the pallet 302; (4) identification of the automated dispensing device 130 at which such containers will be filled; and/or (5) identification of the cap device 138 at which such containers 304 will be capped. Other factors may be employed in determining which orders, or portions thereof, will be filled using a particular pallet 302. Such factors may be applied serially or may be otherwise applied. For example order prioritization module 1302 may present a set of orders (e.g., a set of orders for which more than one pallet 302 may be employed to transport containers) and the pallet selection module 1306 may select from such set of orders (based on one or more of the factors listed above and/or based on other factors) to identify the member or members of the set to be filled using the pallet 302 to transport the containers 304.

The pallet configuration module 1308 may associate particular cavities 306 within a particular pallet 302 with a particular group or a component of an order. Selections may be made by the pallet configuration module 1308 from the orders (or portions of orders) identified as to be filled using the particular pallet 302, e.g., selections made by the pallet selection module 1306. For example the pallet configuration module 1308 may associate a first cavity 306 with a first component of an order (e.g., an order for a particular type and quantity of a pharmaceutical) and may associate a second cavity 306 with a second component of an order. All or less than all of the cavities 306 of the pallet 302 may be associated with a particular component of an order. Association of a particular cavity 306 with a particular order component may be based on one or more than one of: (1) minimizing the changes to the current puck configuration of the pallet 302; (2) consolidating sizes of the pucks 308 or the cavities 306 with no pucks within regions of the pallet 302; and/or (3) optimizing operations at one or more than one of the loading devices 124, the inspect devices 126, the automated dispensing devices 130, the manual dispensing devices 132, the review devices 134, the imaging devices 136, the cap devices 138, the accumulation devices 140, and/or other devices. For example, the cavities 306 may be selected to consolidate containers 304 to be capped with a particular type of cap within one or more than one rows of the pallet 302. Other factors may be employed in configuring a particular pallet 302. In some embodiments, more than one pallet 302 is employed in connection with filling a particular order, such that a cavity 306 on a first pallet 302 may be associated with a first component of an order and a cavity 306 on a second pallet 302 may be associated with a second component of an order.

The pallet configuration module 1308 may control operations of a pucking station 702 to, for example, cause the robot arm 724 to remove one or more than one of the pucks 308 from the pallet 302 retained within the pucking station 702, to place one or more than one of the pucks 308 onto the puck conveyors 718, 720, to retrieve one or more of the pucks 308 (e.g., one or more pucks 308 of a particular size) from the puck holding areas 734, 736 and/or place one or more the one of the pucks 308 into the pallet 302 retained within the pucking station 702. In an embodiment of the pallet sizing and pucking subsystem 204 that includes more than one pucking stations (e.g., the pucking stations 704a, 704b, 704c), the pallet configuration module 1308 may control the operations of one or more of the pucking stations 704a, 704b, 704c to configure the pallet 302 with pucks 308 (e.g., as discussed in further detail above).

Figure 14:
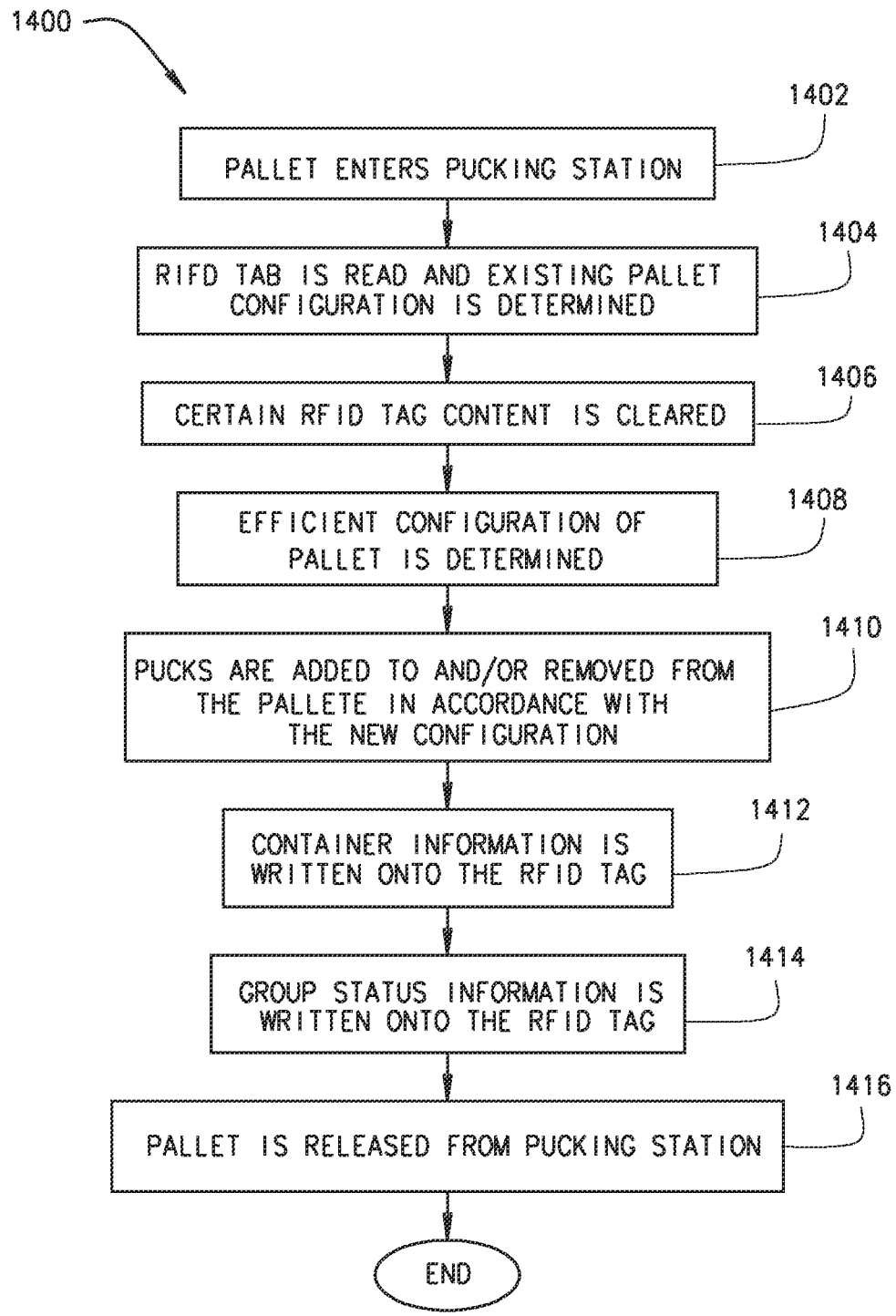
FIG. 14 is an example process flow illustrating a method of controlling the operation of a pallet and pucking device, according to an example embodiment.

FIG. 14 illustrates a method of controlling the operation of a pucking station 702 according to an example embodiment. The method 1400 may be performed by the pallet sizing and pucking device 122, partially by the order processing device 102 and partially by the pallet sizing and pucking device 122, or may be otherwise performed.

At block 1402, a pallet 302 containing pucks 308 enters a pucking station 702 of a pallet sizing and pucking subsystem 204. At block 1404, the existing configuration of the pucks 308 on the pallet 302 is determined based on information read from the RFID tag 314. At block 1406, content of the RFID tag 314, other than the pallet identifier, the number of first-sized pucks, e.g., 75 cc pucks, and the number of second-sized pucks, e.g., 120 cc pucks, is erased. An efficient pucking configuration is determined at block 1408, based on the information read from the RFID tag 314 and/or new data. Efficient fulfillment of the pharmaceutical orders may include optimizing operations at one or more than one of the loading device 124, the inspect device 126, the automated dispensing device 130, the manual fulfillment device 132, the review device 134, the imaging device 136, the cap device 138, or the accumulation device 140. In an example embodiment, efficient fulfillment of the pharmaceutical orders may be based on minimizing the changes to a current puck configuration of the pallet 302. In this case, the least amount of puck movement to and from the pallet 302 is achieved, which may result in the pallet 302 spending a least or lesser amount of time at the pallet sizing and pucking device 122. Orders assigned to the pallet 302 may be determined by the pallet 302 having enough non-assigned pucks 308 to fulfill the prescription order. For example, if a prescription order requires two first sized containers and one second sized container, then the prescription order may be assigned to a single pallet 302 that has unassigned pucks 308 for two first containers and one second container. If the pallet 302 has less than two first container sized pucks 308, then the prescription order may be assigned to another pallet 302 or the pallet configuration must be changed. The pucks 308 are added to and/or removed from the pallet 302 in accordance with the determined configuration at block 1410. At block 1412, container information (such as information about the order associated with a container to be placed in a particular position on the pallet) is modified into a format to be written onto the RFID tag 314 by the pucking station RFID tag reader 704a, 704b and is written onto the RFID tag 314. At block 1414, the pucking station RFID tag reader 704a, 704b writes group status information to the RFID tag 314 of the pallet. The pallet 302 is released from the pucking station 702 at block 1416.

Figure 15:
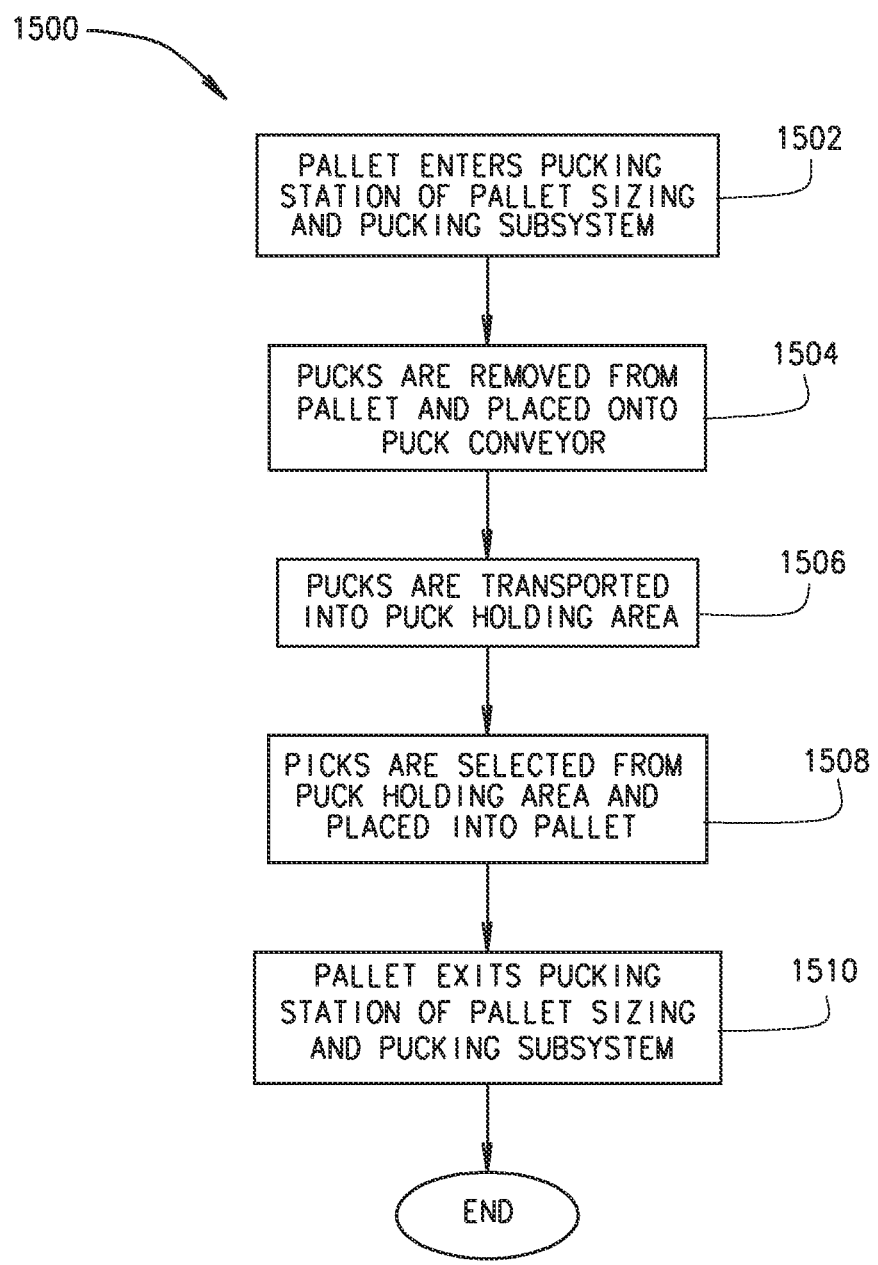
FIG. 15 is an example process flow illustrating a method of configuring a pallet, according to an example embodiment.

FIG. 15 illustrates a method 1500 for configuring a pallet 302 with pucks 308, according to an example embodiment. The method 1500 may be performed by the pallet sizing and pucking device 122, partially by the order processing device 102 and partially by the pallet sizing and pucking device 122, or may be otherwise performed.

At block 1502, a pallet 302 holding containers 304 enters a pucking station 702 of a pallet sizing and pucking subsystem 204. One or more than one pucks 308 are removed from the pallet 302 and placed onto a puck conveyor 718, 720 at block 1504. At block 1506, the pucks 308 are transported into the puck holding areas 734, 736 within the puck conveyor 718, 720. The pucks 308 are selected from the puck holding areas 734, 736 and placed into the pallet 302 at block 1508. After the pallet 302 has been configured at the pucking station 702, it exits the pucking station 702 and the pallet sizing and pucking subsystem 204 at block 1510.

Figure 16:
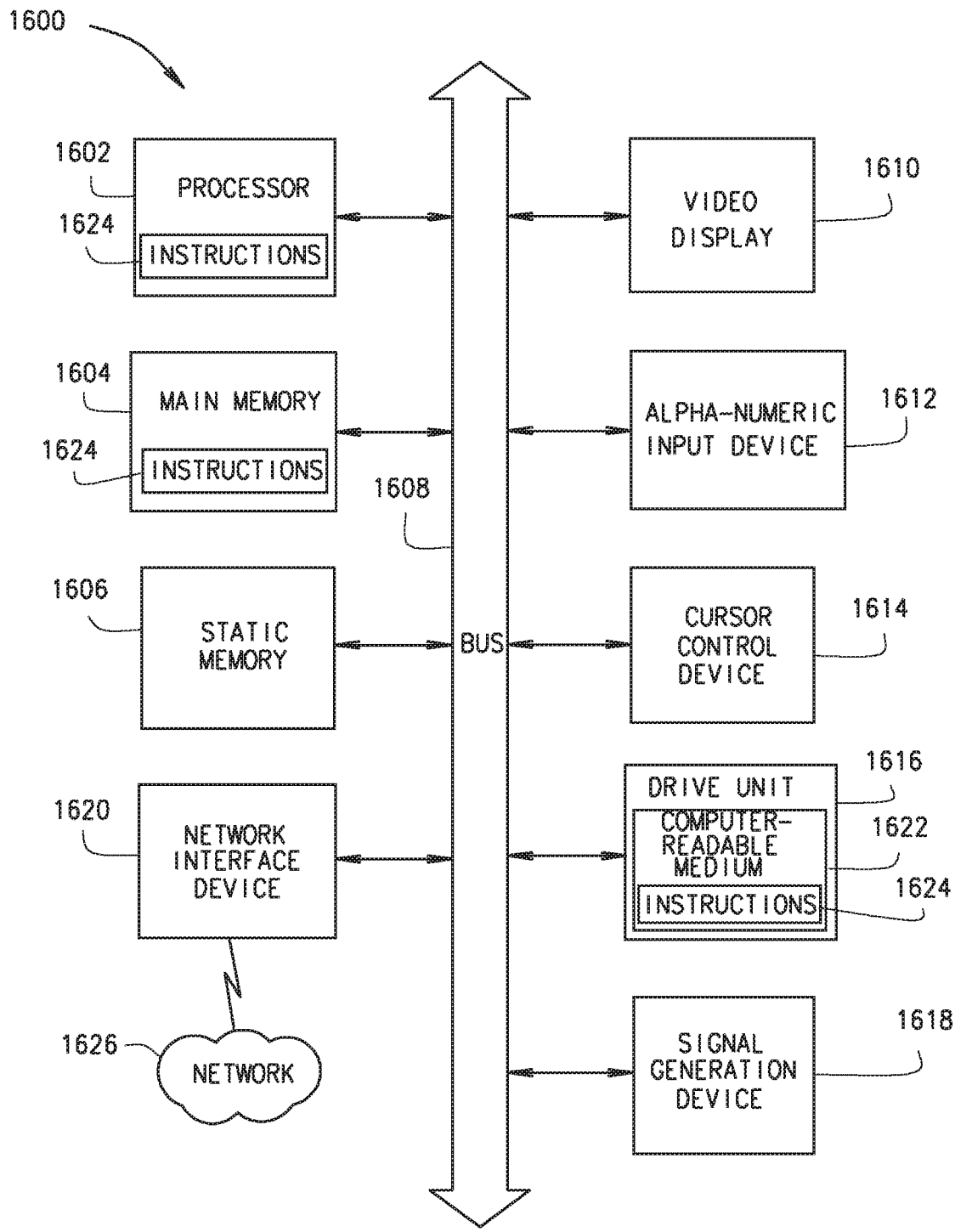
FIG. 16 is a block diagram of a machine in the example form of a computer system within which a set of instructions for causing the machine to perform any one or more of the methodologies discussed herein may be executed or stored.

FIG. 16 shows a block diagram of a machine in the example form of a computer system 1600 within which a set of instructions may be executed causing the machine to perform any one or more of the methods, processes, operations, or methodologies discussed herein. The devices 102, 106, 122-144 may include the functionality of the one or more computer systems 1600.

In an example embodiment, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a server computer, a client computer, a personal computer (PC), a tablet PC, a gaming device, a set-top box (STB), a Personal Digital Assistant (PDA), a cellular telephone, a web appliance, a network router, switch or bridge, or any machine capable of executing a set of instructions sequential or otherwise) that specifies actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 1600 includes a processor 1602 (e.g., a central processing unit (CPU) a graphics processing unit (GPU) or both), a main memory 1604 and a static memory 1606, which communicate with each other via a bus 1608. The computer system 1600 further includes a video display unit 1610 (e.g., a liquid crystal display (LCD), electronic paper or a cathode ray tube (CRT)). The computer system 1600 also includes an alphanumeric input device 1612 (e.g., a keyboard), a cursor control device 1614 (e.g., a mouse), a drive unit 1616, a signal generation device 1618 (e.g., a speaker) and a network interface device 1620.

The drive unit 1616 includes a computer-readable medium 1622 on which is stored one or more sets of instructions (e.g., software 1624) embodying any one or more of the methodologies or functions described herein. The software 1624 may also reside, completely or at least partially, within the main memory 1604 and/or within the processor 1602 during execution thereof by the computer system 1600, the main memory 1604 and the processor 1602 also constituting computer-readable media.

The software 1624 may further be transmitted or received over a network 1626 via the network interface device 1620.

While the computer-readable medium 1622 is shown in an example embodiment to be a single medium, the term "computer-readable medium" should be taken to include a single medium or multiple media (e.g., a centralized or distributed database, and/or associated caches and servers) that store the one or more sets of instructions. The term "computer-readable medium" shall also be taken to include any medium that is capable of storing or encoding a set of instructions for execution by the machine and that cause the machine to perform any one or more of the methodologies of the present invention. The term "computer-readable medium" shall accordingly be taken to include, but not be limited to, solid-state memories, and optical media, and magnetic media. In some embodiments, the computer-readable medium is a non-transitory computer-readable medium.

The term "based on" or using, as used herein, reflects an open-ended term that can reflect others elements beyond those explicitly recited.

Certain the systems, apparatus, applications or processes are described herein as including a number of modules. A module may be a unit of distinct functionality that may be presented in software, hardware, or combinations thereof. When the functionality of a module is performed in any part through software, the module includes a computer-readable medium. The modules may be regarded as being communicatively coupled.

The inventive subject matter may be represented in a variety of different embodiments of which there are many possible permutations.

In an example embodiment, an order processing device receives pharmaceutical orders. A pallet sizing and pucking device is communicatively coupled to the order processing device. The pallet sizing and pucking device configures a pallet with a plurality of pucks. A puck of the plurality of pucks is adapted to receive a container associated with a pharmaceutical order. The pallet sizing and pucking device is configured to perform puck circulation among a plurality of pucking stations.

In another example embodiment, an order processing device receives a pharmaceutical order and associates a container with the pharmaceutical order. A pallet sizing and pucking device is communicatively coupled to the order processing device and includes a control system to select a pallet to use in fulfilling the pharmaceutical order and to select a position on the pallet to receive a puck adapted to receive the container. The pallet sizing and pucking device also includes a pallet sizing and pucking subsystem with a plurality of pucking stations and is configured to circulate a plurality of pucks among the pucking stations, to retain the pallet within a pucking station, and to place the puck selected from among the plurality of pucks at the selected position on the pallet while the pallet is retained in the pucking station.

In yet another example embodiment, a pharmaceutical order processing device processes orders to be filled using containers. A pallet sizing and pucking device is communicatively connected to the order processing device and includes control subsystem to receive a configuration preference from the order processing device. The pallet sizing pucking device also includes a pallet sizing and pucking subsystem to configure a pallet with pucks adapted to receive the containers according to the configuration preference, The pallet sizing and pucking subsystem includes a puck conveyor to circulate pucks among a plurality of pucking stations, each of which has a robot arm to selectively place the pucks onto the pallet and remove the pucks from the pallet. Each robot arm includes a gripper assembly.

Thus, methods and systems for pallet sizing and pucking have been described. Although embodiments of the present invention have been described with reference to specific example embodiments, it will be evident that various modifications and changes may be made to these embodiments without departing from the broader spirit and scope of the embodiments of the invention. Accordingly, the specification and drawings are to be regarded in an illustrative rather than a restrictive sense.

The methods described herein do not have to be executed in the order described, or in any particular order. Moreover, various activities described with respect to the methods identified herein can be executed in serial or parallel fashion. Although "End" blocks are shown in the flowcharts, the methods may be performed continuously.

In the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

What is claimed:

1. A system comprising:
 a gripper assembly including a plurality of gripper heads, a gripper head of the plurality of gripper heads being adapted to grip and to release a puck of a plurality of pucks, and the gripper head being an independently actuated;
 at least two puck holding areas associated with at least two of a plurality of pucking stations;
 at least two of the pucking stations including robot arms and readers, the robot arms being adapted to selectively place the puck onto a container carrier and to selectively remove the puck from the container carrier, the robot arms being further adapted to selectively remove the puck from the puck holding area when the puck is gripped by the gripper assembly and to selectively place the puck over a cavity of a plurality of cavities of the container carrier when the puck is released by the gripper assembly, and the readers being adapted to identify the container carrier and at least one puck therein; and
 a plurality of puck conveyors adapted to circulate the plurality of pucks among and between the plurality of pucking stations, the plurality of puck conveyors including a first puck conveyor and a second puck conveyor, the first puck conveyor being adapted to circulate a first group of the plurality of pucks, the second puck conveyor being adapted to circulate a second group of the plurality of pucks, the first group of the plurality of pucks adapted to receive a first set of containers, and the second group of the plurality of pucks adapted to receive a different second set of containers,
 the robot arms being adapted to selectively place both of the first group of pucks and the second group of pucks into the cavities of the container carrier,
 wherein the plurality of gripper heads are adapted to align with a row of cavities of the plurality of cavities,
 wherein the at least two puck holding areas include a portion of the plurality of puck conveyors, and
 in at least one of the holding areas, the puck conveyors including stop units adapted to activate to hold the pucks in the respective holding area and deactivate to allow the pucks to move along the respective puck conveyors to another holding area.

2. The system of claim 1, wherein each puck of the plurality of pucks is either from the first group of the plurality of pucks or the second group of the plurality of pucks.

3. The system of claim 1, wherein the robot arm is further adapted to selectively place a group of the plurality of pucks onto a row of cavities of the plurality of cavities.

4. The system of claim 1, wherein the plurality of pucking stations are further adapted to configure the container carrier in association with a plurality of pharmaceutical orders.

5. The system of claim 1, wherein the gripper head is a spring assist closed gripper head.

6. The system of claim 1, wherein the gripper head is a spring assist open gripper head.

7. The system of claim 1, wherein the container carrier is a pallet including a non-contact identifier that can be read by the reader.

8. The system of claim 7, wherein the plurality of cavities are in a five-by-five cavity row/column configuration with the pallet.

9. The system of claim 1, wherein the puck is retained over the cavity being placed on an insert extending from and forming the cavity, the insert once place fitting between an interior wall and exterior wall of the puck.

10. The system of claim 1, wherein:
the readers include RFID readers and are adapted to read puck data from a RFID tag associated with the container carrier,
wherein placement of the puck onto the container carrier is based on the puck data.

11. The system of claim 7, further comprising:
a system conveyor to provide the container carrier towards the plurality of pucking stations;
an in-bound lift and transfer unit to move the pallet from the system conveyor to a container carrier conveyor; and
the container carrier conveyor being adapted to receive the container carrier from the in-bound lift and transfer unit and deliver the container carrier through a frame portion of a pucking station of the plurality of pucking stations.

12. The system of claim 1, wherein the pucking station includes a frame portion that supports the robot arm within the pucking station and a portion of the plurality of puck conveyors disposed within the frame portion.

13. A method comprising:
circulating a plurality of pucks using a plurality of puck conveyors that extend through and between a plurality of pucking stations, the plurality of puck conveyors including a first puck conveyor and a second puck conveyor, the first puck conveyor being adapted to circulate a first group of the plurality of pucks, the second puck conveyor being adapted to circulate a second group of the plurality of pucks, the first group of the plurality of pucks being adapted to receive a first set of containers, the second group of the plurality of pucks being adapted to receive a second set of containers, at least two pucking stations of the plurality of pucking stations including robot arms, and at least two of the pucking stations including stop units for selectively holding the pucks in holding areas of the respective pucking stations;
reading a container carrier to identify the container carrier and to assign selected ones of the first group of the plurality of pucks and the second group of the plurality of pucks to the identified container carrier;
activating at least one stop unit to hold at least one puck of the plurality of pucks within the holding area of one of the pucking stations;
selectively placing, using one of the robot arms, a puck of the at least one puck being held by the holding unit in the holding area over a cavity of a plurality of cavities of a container carrier when the puck is released by a gripper assembly, the gripper assembly including a plurality of gripper heads, a gripper head of the plurality of gripper heads adapted to grip and to release the puck, the gripper head being an independently actuated, pneumatic gripper head adapted to grip and to release the puck;
selectively removing, using the robot arm, the puck of the plurality of pucks from the container carrier when the puck is gripped by the gripper assembly; and
deactivating the at least one stop unit to allow the pucks to move along the respective puck conveyors between the pucking stations.

14. The method of claim 13, wherein reading includes reading, using an RFID reader communicatively coupled with a pucking station of the plurality of pucking stations, puck data from an RFID tag associated with the container carrier, wherein placement of the puck onto the pallet is based on the puck data.

15. The method of claim 13 wherein after the puck is retained over the cavity by an insert which extends from the cavity.

16. The method of claim 13 wherein the container carrier is a pallet.

17. The method of claim 13 wherein selectively placing includes placing the puck of the plurality of pucks into the cavity of the plurality of cavities of the container carrier on a row by row basis.

18. The method of claim 13 wherein selectively placing includes operating the gripper head against a spring urging the gripper head closed to open the gripper head.

19. The method of claim 13 wherein selectively placing includes operating the gripper head against a spring urging the gripper head open to close the gripper head.

20. The method of claim 13 wherein reading includes reading at least one of a container carrier identifier, container properties, a number of pucks of the first group of the plurality of pucks to be placed on the container carrier, and a number of pucks of the second group of the plurality of pucks to be placed on the container carrier.

* * * * *